United States Patent
Cirit et al.

(10) Patent No.: US 11,738,340 B2
(45) Date of Patent: Aug. 29, 2023

(54) NEURODEGENERATIVE TARGET DISCOVERY PLATFORM

(71) Applicant: Javelin Biotech, Inc., Woburn, MA (US)

(72) Inventors: Murat Cirit, Cambridge, MA (US); Begum Alaybeyoglu, Cambridge, MA (US); Jason Samuel Sherfey, Somerville, MA (US); John Wayne Rumsey, Somerville, MA (US); Yoojin Shin, Burlington, MA (US)

(73) Assignee: Javelin Biotech, Inc., Woburn, MA (US)

( * ) Notice: Subject to any disclaimer, the term of this patent is extended or adjusted under 35 U.S.C. 154(b) by 205 days.

(21) Appl. No.: 17/063,073

(22) Filed: Oct. 5, 2020

(65) Prior Publication Data

US 2021/0101146 A1 Apr. 8, 2021

Related U.S. Application Data

(60) Provisional application No. 63/034,260, filed on Jun. 3, 2020, provisional application No. 62/910,996, filed on Oct. 4, 2019.

(51) Int. Cl.
*C12N 15/10* (2006.01)
*B01L 3/00* (2006.01)
(Continued)

(52) U.S. Cl.
CPC ....... *B01L 3/502715* (2013.01); *C12M 23/16* (2013.01); *G01N 33/5058* (2013.01);
(Continued)

(58) Field of Classification Search
CPC ....... B01L 3/502715; B01L 2300/0816; B01L 2300/0858; B01L 2300/0861;
(Continued)

(56) References Cited

U.S. PATENT DOCUMENTS

2003/0152646 A1* 8/2003 Longo ................ G01N 33/5058
424/718
2011/0154655 A1 6/2011 Hetke et al.
(Continued)

FOREIGN PATENT DOCUMENTS

WO WO 2013/116834 8/2013
WO WO 2015/157390 10/2015

OTHER PUBLICATIONS

Adams et al., "Oxygen free radicals and Parkinson's disease," Free Radic. Biol. Med., 1991; 10(2):161-9.
(Continued)

*Primary Examiner* — Jennifer Wecker
*Assistant Examiner* — Oyeleye Alexander Alabi
(74) *Attorney, Agent, or Firm* — Fish & Richardson P.C.

(57) ABSTRACT

A microphysiological system (MPS) includes at least one first inlet for receiving a fluid medium. The MPS includes a brain module comprising brain tissue. The MPS includes a blood-brain-barrier (BBB) module comprising BBB tissue, the BBB module configured to receive the fluid medium. The MPS includes a crosstalk channel between the brain module and the BBB module, the crosstalk channel configured to promote a bidirectional crosstalk between the brain tissue and the BBB tissue in response to receiving the fluid medium at the BBB module. The MPS is configured for treating the brain tissue and the BBB tissue with a drug or a combination of drugs to determine a phenotypic effect and a transcriptomic effect of the drug. A drug perturbation is related to the phenotypic effect and the transcriptomic effect based on kinetic optimization.

14 Claims, 19 Drawing Sheets

(51) Int. Cl.
| | |
|---|---|
| G01N 21/3504 | (2014.01) |
| G01N 33/00 | (2006.01) |
| G01N 33/574 | (2006.01) |
| G01N 21/64 | (2006.01) |
| A61K 45/06 | (2006.01) |
| G01N 21/35 | (2014.01) |
| G01N 33/50 | (2006.01) |
| G01N 33/543 | (2006.01) |
| B01L 3/02 | (2006.01) |
| G01N 33/53 | (2006.01) |
| C12M 3/06 | (2006.01) |

(52) U.S. Cl.
CPC .......... B01L 2300/0816 (2013.01); B01L 2300/0858 (2013.01); B01L 2300/0861 (2013.01); B01L 2300/123 (2013.01); G01N 2570/00 (2013.01)

(58) Field of Classification Search
CPC ....... B01L 2300/123; B01L 2300/0645; B01L 2300/0681; B01L 2300/069; B01L 3/502761; C12M 23/16; C12M 35/08; G01N 33/5058; G01N 2570/00; G16B 25/10; G16B 40/10; G16H 20/10; G16H 50/70
See application file for complete search history.

(56) References Cited

U.S. PATENT DOCUMENTS

| | | | | |
|---|---|---|---|---|
| 2013/0203086 | A1* | 8/2013 | Achyuta | G01N 33/5058 435/7.1 |
| 2014/0142370 | A1 | 5/2014 | Wong et al. | |
| 2015/0031116 | A1 | 1/2015 | Quake et al. | |
| 2017/0015964 | A1* | 1/2017 | Agabi | C12M 23/34 |
| 2021/0324316 | A1* | 10/2021 | Daniele | C12M 25/14 |

OTHER PUBLICATIONS

Akiyama et al., "Microglial response to 6-hydroxydopamine-induced substantia nigra lesions," Brain Research, 1989, 489(2): 247-253.
Andersen et al., "Cerebrospinal fluid biomarkers for Parkinson's disease—a systematic review," Acta Neurol. Scand., 2017, 135(1):34-56, 23 pages.
Assal et al., "Tolcapone and fulminant hepatitis," Lancet., 1998; 352: 1 page.
Azdad et al., "Homeostatic Plasticity of Striatal Neurons Intrinsic Excitability following Dopamine Depletion," PLoS One, 2009; 4(9): 12 pages.
Azevedo et al., "Equal numbers of neuronal and nonneuronal cells make the human brain an isometrically scaled-up primate brain," J. Comp. Neurol., 2009; 513(5):532-41.
Babic et al., "Parkinson's Disease-Challenges in New Drug Development," Coll. Antropol., 2008; 32(4):1275-81., 7 pages.
Bai et al., "Translational Quantitative Systems Pharmacology in Drug Development: from Current Landscape to Good Practices," AAPS J., 2019; 21(4):72.
Beaulieu et al., "The Physiology, Signaling, and Pharmacology of Dopamine Receptors," Pharmacol Rev., 2011; 63(1):182-217.
Blesa et al., "Classic and New Animal Models of Parkinson's Disease," J. Biomed. Biotechnol., 2012, Article: 845618, 11 pages.
Blesa et al., "Parkinson's disease: animal models and dopaminergic cell vulnerability," Front. Neuroanat, 2014, 8:155, 12 pages.
Blum et al., "Molecular pathways involved in the neurotoxicity of 6-OHDA, dopamine and MPTP: contribution to the apoptotic theory in Parkinson's disease," Prog. Neurobiol., 2001; 65(2): 135-72.
Bogdanov et al., "Metabolomic profiling to develop blood biomarkers for Parkinson's disease," Brain, 2008; 131(Pt 2):389-96.
Booth et al., "The Role of Astrocyte Dysfunction in Parkinson's Disease Pathogenesis," 2017, 40(6):358-370.
Borrageiro et al., "A review of genome-wide transcriptomics studies in Parkinson's disease," Eur. J. Neurosci., 2018; 47(1):1-16.
Bradshaw et al., Applications of Quantitative Systems Pharmacology in Model-Informed Drug Discovery: Perspective on Impact and Opportunities, CPT Pharmacometrics Syst. Pharmacol., 2019; 8: 777-791.
Brochard et al., "Infiltration of CD4+ lymphocytes into the brain contributes to neurodegeneration in a mouse model of Parkinson disease," J. Clin. Invest., 2009: 119(1):182-192.
Brown et al., "Physiological Parameter Values for Physiologically Based Pharmacokinetic Models." Toxicol. Ind. Health., 1997; 13(4):407-84.
Bushel et al. "A Comparison of the TempO-Seq S1500+ Platform to RNA-Seq and Microarray Using Rat Liver Mode of Action Samples," Front. Genet., 2018; 9(485) 39 pages.
Carcamo-Orive et al., "Analysis of Transcriptional Variability in a Large Human iPSC Library Reveals Genetic and Non-genetic Determinants of Heterogeneity" Cell Stem Cell, 2017; 20(4):518-32, 25 pages.
Carvey et al., "6-Hydroxydopamine-induced alterations in blood-brain barrier permeability," Eur. J. Neurosci., 2005; 22(5):1158-68.
Centonze et al., "Dopamine D2 receptor-mediated inhibition of dopaminergic neurons in mice lacking D2L receptors," Neuropsychopharmacology, 2002; 27(5):723-6.
Chang et al., "Alternations of Metabolic Profile and Kynurenine Metabolism in the Plasma of Parkinson's Disease." Mol. Neurobiol., 2018; 55(8):6319-28.
Chen et al., "Integrated gut/liver microphysiological systems elucidates inflammatory inter-tissue crosstalk," Biotechnol Bioeng., 2017; 114(11):2648-59.
Chen et al., "Longitudinal Metabolomics Profiling of Parkinson's Disease-Related alpha-Synuclein A53T Transgenic Mice," PLoS One, 2015; 10(8).
Chen JJ., "Pharmacologic Safety Concerns in Parkinson's Disease: Facts and Insights," Int. J. Neurosci., 2011; 121:Suppl 2:45-52.
Chong et al., "MetaboAnalyst 4.0: towards more transparent and integrative metabolomics analysis," Nucleic Acids Res., 2018; 46: 9 pages.
Cirit et al., "Maximizing the Impact of Microphysiological Systems with In vitro-In vivo Translation," Lab Chip., 2018, 18(13):1831-7, 7 pages.
Cook et al., "Lessons learned from the fate of AstraZeneca's drug pipeline: a five-dimensional framework," Nat. Rev. Drug Discov., 2014; 13(6):419-31.
Costa et al., "Diagnostic validity of biomarkers in Parkinson's Disease: systematic review and meta-analysis," Rev. Bras. Enferm., 2018, 71(6):3074-83, 10 pages.
Dawson et al., "Genetic Animal Models of Parkinson's Disease," Neuron., 2010. 66(5):646-61, 16 pages.
Desai et al., "Blood-Brain Barrier Pathology' in Alzheimer's and Parkinson's Disease: Implications for Drug Therapy," Cell Transplant. 2007; 16(3): 285-299.
Devine et al., "Parkinson's disease induced pluripotent stem cells with triplication of the alpha-synuclein locus," Nat. Commun., 2011; 2(1): 10 pages.
Domenico et al., "Patient-Specific iPSC-Derived Astrocytes Contribute to Non-Cell-Autonomous Neurodegeneration in Parkinson's Disease," Stem Cell Report, Feb. 2019, 12(2):213-229.
Dorato et al. "The no-observed-adverse-effect-level in drag safety evaluations: use, issues, and definition(s)," Regul. Toxicol. Pharmacol., 2005; 42(3):265-74.
Duty et al., "Animal models of Parkinson's disease: a source of novel treatments and clues to the cause of the disease," Br. J. Pharmacol., 2011, 164(4):1357-91, 35 pages.
Edington et al., "Interconnected Microphysiological Systems for Quantitative Biology and Pharmacology Studies," Sci. Rep., 2018; 8(1):4530, 18 Pages.
Ekblom et al., "Monoamine oxidase-B in astrocytes," Glia., 1993; 8(2):122-32.

(56) References Cited

OTHER PUBLICATIONS

Ellis et al., "Current approaches to the treatment of Parkinson's Disease," Bioorg. Med. Chem. Lett., 2017, 27(18):4247-55, 9 pages.
Erro et al., "The Heterogeneity of Early Parkinson's Disease: A Cluster Analysis on Newly Diagnosed Untreated Patients," PLoS One, 2013, 8(8), 8 pages.
Falkenburger et al., "Cellular models for Parkinson's disease," J. Neurochem., 2016, 139(1):121-30, 10 pages.
Farmer et al., "Major Alterations of Phosphatidylcholine and Lysophosphotidylcholine Lipids in the Substantia Nigra Using an Early Stage Model of Parkinson's Disease," Int. J. Mol. Sci., 2015; 16(8):18865-77.
Ferre et al., "Adenosine-dopamine receptor-receptor interactions as an integrative mechanism in the basal ganglia," Trends in Neurosci., 1997; 20(10):482-7.
Foltynie et al., "The heterogeneity of idiopathic Parkinson's disease," J Neurol, 2002; 249(2):138-45, 8 pages.
Fowler et al., "The effect of age on the activity and molecular properties of human brain monoamine oxidase," J. Neural Transm., 1980; 49(1-2):1-20.
Gagnon et al. "Striatal Neurons Expressing D1 and D2 Receptors are Morphologically Distinct and Differently Affected by Dopamine Denervation in Mice," Sci. Rep., 2017: 7: 16 pages.
Gao et al., "Why neurodegenerative diseases are progressive: uncontrolled inflammation drives disease progression." Trends Immunol., 2008; 29(8):357-65.
Gelb et al., "Diagnostic Criteria for Parkinson disease," Arch. Neurol., 1999; 56(1):33-9.
Gjedde et al., "Striatal L-DOPA Decarboxylase Activity in Parkinson's Disease in Vivo: Implications for the Regulation of Dopamine Synthesis," J. Neurochem., 1993; 61(4):1538-41.
Graffmann et al. "Modeling Nonalcoholic Fatty Liver Disease with Human Pluripotent Stem Cell-Derived Immature Hepatocyte-Like Cells Reveals Activation of PLIN2 and Confirms Regulatory Functions of Peroxisome Proliferator-Activated Receptor Alpha," Stem. Cells Dev., 2016; 25(15):1119-33.
Greenland et al., "The clinical heterogeneity of Parkinson's disease and its therapeutic implications," Eur J Neurosci., 2019;49(3):328-38, 16 pages.
Groppetti et al. "Dopamine receptor changes in response to prolonged treatment with L-dopa," J. Neural. Transm. Suppl., 1986; 22:33-45.
Halliwell B., "Reactive Oxygen Species and the Central Nervous System," J. Neurochem., 1992; 59(5):1609-23.
Hamadjida et al., "Classic Animal Models of Parkinson's Disease: a Historical Perspective," Behav. Pharmacol., 2019, 30(4):291-310, 20 pages.
Hawkins et al., "An active transport system in the blood-brain barrier may reduce levodopa availability," Exp, Neurol., 2005; 195(1):267-71.
Herculano-Houzel S., "The human brain in numbers: a linearly scaled-up primate brain," Frontiers in Human Neuroscience, 2009; 3:31, 11 pages.
Hirsch et al. "Neuroinflammation in Parkinson's disease: a target for neuroprotection?" Lancet Neurol., 2009, 8(4):382-97, 16 pages.
Hirsch et al., "Nondopaminergic neurons in Parkinson's disease,"Adv. In Neurol., 2003; 91:29-37.
Hollmann et al., "Accelerated differentiation of human induced pluripotent stem cells to blood-brain barrier endothelial cells," Fluids Barriers CNS, 2017; 14(1):9.
Hu et al., "Neural differentiation of human induced pluripotent stem cells follows developmental principles but with variable potency," Proc Natl Acad Sci USA, 2010;107(9):4335-40, 6 pages.
Isoherranen et al., "Emerging Role of Organ-on-a-Chip Technologies in Quantitative Clinical Pharmacology Evaluation," Clin. Transl. Sci., 2019; 12(2):113-21.
Jaber et al., "Dopamine receptors and brain function," Neuropharmacology, 1996; 35(11):1503-19.
Jankovic et al., "Current approaches to the treatment of Parkinson's disease," Neuropsychiatr. Dis. Treat., 2008, 4(4):743-57, 16 pages.
Johnson, D.E., "Biotherapeutic first-in-human dose selection: making use of preclinical markers," Expert Rev. Clin. Pharmacol., 2010; 3(2):231-42.
Kamburov et al., "Integrated pathway-level analysis of transcriptomics and metabolomics data with IMPaLA," Bioinformatics, 2011; 27(20):2917-8.
Kaushik et al., "Quantitative Label-Free Imaging of 3D Vascular Networks Self-Assembled in Synthetic Hydrogels," Adv Healthc Mater, 2019; 8(2), 12 pages.
Kelly et al., "Gene expression meta-analysis of Parkinson's disease and its relationship with Alzheimer's disease," Mol. Brain., 2019;12(1): 10 pages.
Koiagar et al., "Human Pluripotent Stem Cells in Neurodegenerative Diseases: Potentials, Advances, and Limitations," Curr. Stem Cell Res. Ther., 2019: 9 pages.
Koprich et al., "Neuroinflammation mediated by IL-1beta increases susceptibility of dopamine neurons to degeneration in an animal model of Parkinson's disease," J Neuroinflammation, 2008;5:8, 12 pages.
Kuzumaki et al., "Cell-specific overexpression of COMT in dopaminergic neurons of Parkinson's disease," Brain., 2019; 142(6): 15 pages.
Lazaro et al., "Cellular models as tools for the study of the role of alpha-synuclein in Parkinson's Disease" Exp. Neurol., 2017, 298(Pt. B):162-71, 10 pages.
Lee et al., "Animal models of Parkinson's disease: vertebrate genetics," Cold Spring Harb Perspect Med., 2012, 2(10), 14 pages.
Lees et al., "Parkinson's Disease" Lancet, 2009, 373(9680):2055-66, 12 pages.
Levey et al., "Localization of D1 and D2 dopamine receptors in brain with subtype-specific antibodies," Proc. Natl. Acad. Sci.,1993; 90(19):8861-5.
Levitt et al., "Immunocytochemical demonstration of monoamine oxidase B in brain astrocytes and serotonergic neurons," Proc. Natl. Acad. Sci., 1982; 79(20):6385-9.
Lewis et al., "Heterogeneity of Parkinson's disease in the early clinical stages using a data driven approach," J Neurol Neurosurg Psychiatry., 2005; 76(3):343-8, 6 pages.
Lewitt et al., "3-Hydroxykynurenine and other Parkinson's Disease Biomarkers Discovered by Metabolomic Analysis," Mov. Disord., 2013; 28(12):1653-60.
Li et al., "A "middle-out" approach to human pharmacokinetic predictions for OATP substrates using physiologically-based pharmacokinetic modeling," J. Pharmacokinet. Pharmacodyn., 2014; 41(3):197-209.
Li et al., "Prioritizing Parkinson's disease genes using population-scale transcriptomic data," Nat. Commun., 2019; 10(1): 10 pages.
Lippmann et al., "Derivation of blood-brain barrier endothelial cells from human pluripotent stem cells," Nat. Biotechnol., 2012; 30(8):783-91.
Love et al., "Moderated estimation of fold change and dispersion for RNA-seq data with DESeq2," Genome Biol., 2014; 15(12): 21 pages.
Ma et al., "Deterministically patterned biomimetic human iPSC-derived hepatic model via rapid 3D bioprinting," Proc. Natl. Acad. Sci., 2016; 113(8):2206-11.
Maass et al., "Establishing quasi-steady state operations of microphysiological systems (MPS) using tissue-specific metabolic dependencies," Sci Rep., 2018;8(1):8015, 13 pages.
Maass et al., "Multi-functional scaling methodology for translational pharmacokinetic and pharmacodynamic applications using integrated microphysiological systems (MPS)," Integr. Biol., 2017;9(4):290-302, 13 pages.
Maass et al., "Translational Assessment of Drug-Induced Proximal Tubule Injury Using a Kidney Microphysiological System," CPT Pharmacometrics Syst. Pharmacol., 2019, 8(5):316-25, 10 pages.
Mahar Doan et al., "Passive Permeability and P-Glycoprotein-Mediated Efflux Differentiate Central Nervous System (CNS) and Non-CNS Marketed Drugs," J. Pharmacol. Exp. Ther., 2002; 303(3):1029-37.

(56) References Cited

OTHER PUBLICATIONS

Marinova-Mutafchieva et al., "Relationship between microglial activation and dopaminergic neuronal loss in the substantia nigra: a time course study in a 6-hydroxydopamine model of Parkinson's disease," Journal of Neurochem., 2009; 110(3): 966-75.

Marshall et al., "Model-Informed Drug Discovery and Development: Current Industry Good Practice and Regulatory Expectations and Future Perspectives," CPT Pharmacometrics Syst. Pharmacol., 2019; 8(2):87-96.

Martinez-Morales et al., "Stem cells as in vitro model of Parkinson's Disease," Stem Cells Int., 2012, 2012:980941, 8 pages.

Melamed et al., "Nonaminergic striatal neurons convert exogenous L-dopa to dopamine in parkinsonism," Ann. Neurol., 1980; 8(6):558-63.

Miklossy et al., "Role of ICAM-1 in persisting inflammation in Parkinson disease and MPTP monkeys," Exp Neurol., 2006; 197(2):275-83, 9 pages.

Mina et al., "Assessment of Drug-Induced Toxicity Biomarkers in the Brain Microphysiological System (MPS) Using Targeted and Untargeted Molecular Profiling," Frontiers in Big Data, 2019; 2(23), 15 pages.

Mishra et al., "Physiological and Functional Basis of Dopamine Receptors and Their Role in Neurogenesis: Possible Implication for Parkinson's disease," J. Exp. Neurosci., 2018; 12:8 pages.

Morimoto et al., "Establishment and Characterization of Mammalian Cell Lines Stably Expressing Human L-Type Amino Acid Transporters.," J. Pharmacol. Sci., 2008; 108(4):505-16.

Mortimer et al., "Relationship of motor symptoms to intellectual deficits in Parkinson disease," Neurology, 1982, 32(2):133-7, 6 pages.

Moustafa et al., "Motor Symptoms in Parkinson's Disease: A Unified Framework" Neurosci. Biobehav. Rev., 2016, 68:727-40, 14 pages.

Munchau et al., "Pharmacological Treatment of Parkinson's Disease," Postgrad Med. J., 2000. 76(900):602-10, 9 pages.

Munoz et al., "Dopamine oxidation and autophagy," Parkinsons Dis., 2012; 14 pages.

Nalls et al. "Large-scale meta-analysis of genome-wide association data identifies six new risk loci for Parkinson's disease," Nat. Genet., 2014, 46(9):989-9, 7 pages.

Noel et al., "A primary human macrophage-enteroid co-culture model to investigate mucosal gut physiology and host-pathogen interactions," Sci. Rep., 2017; 7: 14 pages.

Nomura et al., "PSA-NCAM distinguishes reactive astrocytes in 6-OHDA-lesioned substantia nigra from those in the striatal terminal fields," Journal of Neuroscience Research, 2000, 61(6): 588-596.

Obach, Prediction of human clearance of twenty-nine drugs from hepatic microsomal intrinsic clearance data: An examination of in vitro half-life approach and nonspecific binding to microsomes. Drug Metab Dispos. 1999;27(11):1350-9.

Oertel "Recent advances in treating Parkinson's disease," F1000Res. 2017, 6:260, 14 pages.

Oertel et al., "Current and experimental treatments of Parkinson disease: A guide for neuroscientists," J. Neurochem., 2016; 139 Suppl 1:325-37.

Ohlin et al., "Vascular endothelial growth factor is upregulated by L-dopa in the parkinsonian brain: implications for the development of dyskinesia," Brain., 2011; 134(Pt 8):2339-57.

Olanow C.W., "Tolcapone and Hepatotoxic Effects," Tasmar Advisory Panel. Arch Neurol., 2000; 57(2):263-7.

Olanow et al., "Etiology and Pathogenesis of Parkinson's Disease" Annu. Rev. Neurosci. 1999, 22:123-44, 23 pages.

Pamies et al., "Rotenone Exerts Developmental Neurotoxicity in a Human Brain Spheroid Model," Toxicol. Appl. Pharmacol., 2018; 354:101-14.

PCT International Search Report and Written Opinion in International Appln. No. PCT/US2020/054286, dated Feb. 11, 2021, 13 pages.

Pelvig et al., "Neocortical glial cell numbers in human brains." Neurobiol. Aging., 2008; 29(11):1754-62.

Peretz et al., "Comparison of Selegiline and Rasagiline Therapies in Parkinson Disease: A Real-life Study," Clin. Neuropharmacol., 2016; 39(5):227-31.

Piccini et al., "The catechol-O-methyltransferase (COMT) inhibitor entacapone enhances the pharmacokinetic and clinical response to Sinemet CR in Parkinson's disease," J. Neurol. Neurosurg. Psychiatry., 2000; 68(5):589-94.

Pinder et al., "Levodopa and Decarboxylase Inhibitors: A Review of their Clinical Pharmacology and Use in the Treatment of Parkinsonism," Drugs, 1976; 11(5):329-77.

Poewe et al., "Parkinson Disease" Nat. Rev. Dis. Primers. 2017, 3:17013, 21 pages.

Raicevic et al., "The Mechanisms of 6-Hydroxydopamine-Induced Astrocyte Death," Annals of the New York Academy, 2005, 1048(1):400-405.

Rappold et al., "Astrocytes and therapeutics for Parkinson's disease," Neurotherapeutics, 2010, 7:413-423, 11 pages.

Reeve et al., "Ageing and Parkinson's Disease: Why is Advancing Age the Biggest Risk Factor?" Ageing Res. Rev., 2014, 14:19-30, 12 pages.

Riederer et al., "Localization of MAO-A and MAO-B in Human Brain: a Step in Understanding the Therapeutic Action of L-Deprenyl," Adv. Neurol., 1987; 45:111-8.

Rizek et al., "An update on the diagnosis and treatment of Parkinson disease," CMAJ, 2016, 188(16):1157-6, 9 pages.

Rodriguez-Pallares et al., "Mechanism of 6-hydroxydopamine neurotoxicity: tire role of NADPH oxidase and microglial activation in 6-hydroxydopamine-induced degeneration of dopaminergic neurons.," J Neurochem., 2007; 103(1):145-56, 12 pages.

Saiki et al., "Decreased long-chain acylcarnitines from insufficient beta-oxidation as potential early diagnostic markers for Parkinson's disease," Sci Rep., 2017; 7(1): 15 pages.

Saiari et al., "In vivo, in vitro and pharmacologic models of Parkinson's disease.," Physiol Res., 2019, 68(1):17-24, 8 pages.

Sarkar et al., "Integrated Assessment of Diclofenac Biotransformation, Pharmacokinetics, and Omics-Based Toxicity in a Three-Dimensional Human Liver-Immunocompetent Coculture System," Drug Metab Dispos., 2017; 45(7):855-66.

Saura et al., "Age-related changes on MAO in B1/C57 mouse tissues: a quantitative radioautographic study," J. Neural. Transm. Suppl. 1994;41:89-94.

Schapira et al., "Etiology and Pathogenesis of Parkinson's Disease," Mov. Disord., 2011, 26(6)4049-55, 7 pages.

Schober, "Classic toxin-induced animal models of Parkinson's disease: 6-0HDA and MPTP," Cell Tissue Res., 2004, 318(1):215-24, 10 pages.

Schwartz et al. "Human pluripotent stem cell-derived neural constructs for predicting neural toxicity," Proc Natl Acad Sci USA, 2015; 112(40):12516-21, 6 pages.

Shao et al., "Recent advances and perspectives of metabolomics-based investigations in Parkinson's disease," Mol. Neurodegener., 2019. 14(1):3, 12 pages.

Sherer et al., "An in vitro model of Parkinson's disease: linking mitochondrial impairment to altered alpha-synuclein metabolism and oxidative damage," J. Neurosci., 2002, 22(16):7006-15, 10 pages.

Sobie et al., "Systems Biology—Biomedical Modeling," Sci. Signal., 2011; 4(190) 6 pages.

Sokoloff et al., "The Dopamine D3 Receptor: A Therapeutic Target for the Treatment of Neuropsychiatric Disorders," CNS Neurol Disord Drug Targets, 2006; 5(1):25-43.

Spence et al., "Directed differentiation of human pluripotent stem cells into intestinal tissue in vitro," Nature., 2011; 470(7332):105-9.

Stack et al., "Therapeutic attenuation of mitochondrial dysfunction and oxidative stress in neurotoxin models of Parkinson's disease," Biochemica et Biophysica Acta—Molecular Basis of Diease, Mar. 2008, 1782(3)151-62.

Stokes et al., "Physiome-on-a-Chip: The Challenge of "Scaling" in Design, Operation, and Translation of Microphysiological Systems" CPT Pharmacometrics Syst. Pharmacol., 2015, 4(10):559-62, 4pages.

(56) References Cited

OTHER PUBLICATIONS

Tan, "Current and emerging treatments in Parkinson's disease" Ann. Acad. Med., 2001, 30(2):128-33, 6 pages.
Tang et al., "Dopamine Receptor-mediated Ca(2+) Signaling in Striatal Medium Spiny Neurons," J. Biol. Chem., 2004; 279(40):42082-94.
Tsamandouras et al., "Integrated Gut and Liver Microphysiological Systems for Quantitative In Vitro Pharmacokinetic Studies," AAPS J., 2017;19(5):1499-512, 14 pages.
Tsamandouras et al., "Quantitative Assessment of Population Variability in Hepatic Drug Metabolism Using a Perfused Three-Dimensional Human Liver Microphysiological," System. J. Pharmacol. Exp. Ther., 2017, 360(1):95-105, 11 pages.
Uchino et al., "Transport of Amino Acid-Related Compounds Mediated by L-Type Amino Acid Transporter 1 (LAT1): Insights Into the Mechanisms of Substrate Recognition.," Mol. Pharmacol., 2002; 61(4):729-37.
Verkhratsky et al., "Neurological diseases as primary gliopathies: a reassessment of neurocentrism." ASN Neuro, 2012; 4(3), 19 pages.
Vindis et al., "Dopamine induces ERK activation in renal epithelial cells through H2O2 produced by monoamine oxidase," Kidney Int., 2001; 59(1):76-86.
Von Bartheld et al., "The search for true numbers of neurons and glial cells in the human brain: A review of 150 years of cell counting," J. Comp. Neurol., 2016; 524(18):3865-95.
Wang et al., "Analysis of an Integrated Human Multiorgan Microphysiological System for Combined Tolcapone Metabolism and Brain Metabolomics," Anal. Chem., 2019; 91(13):8667-75, 9 pages.
Wang et al., "Systems biology and the discovery of diagnostic biomarkers," Dis. Markers., 2010; 28(4):199-207.
Wei et al., "Dopaminergic treatment weakens medium spiny neuron collateral inhibition in the parkinsonian striatum," J. Neurophysiol., 2017; 117(3):987-99.
Westlund et al., "Distinct monoamine oxidase A and B populations in primate brain," Science, 1985; 230(4722):181-3.
Westlund et al., "Localization of distinct monoamine oxidase A and monoamine oxidase B cell populations in human brainstem," Neuroscience, 1988; 25(2):439-56.
Winklhofer et al., "Mitochondrial Dysfunction in Parkinson's Disease" Biochim. Biophys. Acta., 2010, 1802(1):29-44, 16 pages.
Wong et al., "Cytokines, nitric oxide, and cGMP modulate the permeability of an in vitro model of the human blood-brain barrier," Exp. Neurol., 2004; 190(2):446-55.
Workman et al., "Enhanced Utilization of Induced Pluripotent Stem Cell-Derived Human Intestinal Organoids Using Microengineered Chips," Cell. Mol. Gastroenterol. Hepatol., 2018; 5(4):669-77.
Yadav et al., "Recent Advances in the System Biology-based Target Identification and Drug Discovery," Curr. Top. Med. Chem., 2018; 18(20):1737-44.
Yeakley et al., "A trichostatin A expression signature identified by TempO-Seq targeted whole transcriptome profiling," PLoS One, 2017; 12(5): 22 pages.
Yeung et al., "Monoamine Oxidases (MAOs) as Privileged Molecular Targets in Neuroscience: Research Literature Analysis," Front. Mol. Neurosci., 2019; 12(143) 12 pages.
Yu et al., "Quantitative Systems Pharmacology Approaches Applied to Microphysiological Systems (MPS): Data Interpretation and Multi-MPS Integration," CPT Pharmacometrics Syst Pharmacol., Oct. 2015; 4(10):585-94, 10 pages.
Zaja-Milatovic et al., "Dendritic degeneration in neostriatal medium spiny neurons in Parkinson disease," Neurology, 2005; 64(3):545-7.
Zheng et al., "NMR-Based Metabolomics Reveal a Recovery from Metabolic Changes in the Striatum of 6-OHDA-Induced Rats Treated with Basic Fibroblast Growth Factor," Mol. Neurobiol., 2016; 53(10):6690-7.
Zou et al., "Advanced Systems Biology Methods in Drug Discovery and Translational Biomedicine," Biomed Res Int., 2013; 9 pages.
International Preliminary Report on Patentability in International Appln. No. PCT/US2020/054286, dated Apr. 14, 2022, 10 pages.

\* cited by examiner

NEURODEGENERATIVE TARGET DISCOVERY PLATFORM

CLAIM OF PRIORITY

This application claims priority under 35 U.S.C. § 119(e) to provisional U.S. Patent Application Ser. No. 62/910,996, filed on Oct. 4, 2019, and Application Ser. No. 63/034,260, filed on Jun. 3, 2020, the entire contents of which are hereby incorporated by reference.

FIELD OF THE INVENTION

This disclosure generally relates to microfluidic devices. More specifically, this disclosure relates to preclinical drug discovery platforms and processes for neurodegenerative diseases.

BACKGROUND

Central nervous system drugs are medicines that affect the central nervous system (CNS). The CNS is responsible for processing and controlling many bodily functions and includes nerves in the brain and spinal cord. There are many different types of drugs that work on the CNS, including anesthetics, anticonvulsants, antiemetics, antiparkinson agents, CNS stimulants, muscle relaxants, narcotic analgesics (pain relievers), nonnarcotic analgesics (such as acetaminophen and NSAIDs), and sedatives.

The regulatory approval rate for drugs targeting central nervous system (CNS) diseases is much lower than that of other diseases (about 7-8%). A major reason for high attrition rates in CNS drug development is due to the lack of efficacy. Currently, pharmaceutical scientists in preclinical drug discovery rely heavily on in vitro neural cell cultures and in vivo animal models. Such in vitro models generally do not recapitulate cytoarchitectural and chemical signaling complexity of neurodegenerative diseases. Additionally, in vivo animal models generally lack human relevance. Thus, these preclinical models can have limited translational value for drug discovery, especially to identify novel disease targets and to assess mechanism of action of compounds observed in humans.

Parkinson's disease (PD) is the second most common neurodegenerative disease affecting 2-3% of people over 65 years of age. PD is primarily characterized by the loss of dopaminergic (DA) neurons in the substantia nigra pars compacta leading to a dopamine deficit in the striatum. The loss of DA neurons results in a range of motor symptoms including akinesia, bradykinesia, tremors, and rigidity causing gait disturbance, grip force, and speech deficits. While the investigation of the cause of PD has been a focus of the neuroscience field for many decades, recent advances in neuroscience and genetics have improved the understanding of the environmental and genetic factors to develop PD. The most common cause of PD is a complex interaction of environmental and genetic factors, while approximately 10-15% of PD patients have a family history of this disorder. Although age is the main known risk factor, susceptibility genes including genetic mutation on SNCA, LRRK-2, PARK 7, PINK 1, PRKN are associated with familial origin of PD. Additionally, alterations in certain genes, such as GBA and UCHL1 do not cause PD but have appeared to increase the risk of developing the condition. Recent data on non-cell-autonomous pathological mechanisms in PD, which are mostly mediated by activated glial and peripheral immune cells, also supports the multicellular nature of PD progression. These inflammatory responses trigger deleterious events, such as oxidative stress and cytokine-receptor-mediated apoptosis, which might eventually lead to DA cell death and disease progression.

Currently, approved therapies for PD patients aim to increase striatal dopamine levels to improve associated motor deficits. These therapies are dopamine replacement therapy with levodopa (a dopamine precursor), dopamine agonist therapies, which act on dopamine receptors to augment the effects of dopamine, monoamine oxidase-B (MAO-B) and catechol-O-methyltransferase (COMT) inhibitors to increase dopamine levels in the brain, and anticholinergics, which modulate the activity of acetylcholine. The clinical PD treatment strategy depends on the stage of the disease. The most common treatment is levodopa/carbidopa, which is used adjuvant with COMT inhibitors. Early-stage treatments include MAO-B inhibitors, anticholinergics, and dopamine agonists. However, these approaches do not represent a long-term solution, as each loses efficacy as DA neurodegeneration progresses over time.

SUMMARY

This disclosure describes a preclinical drug discovery system for developing treatments (e.g., drugs) for neurodegenerative diseases. The preclinical drug discovery system for neurodegenerative diseases (the system) is configured to merge human complex in vitro models (CIVM) with model-informed drug discovery (MIDD) methodologies. The system that supports the CIVMs includes microfluidic hardware and physiological cytoarchitecture using microphysiological systems (MPSs). The MPSs can form neurovascular units, or NVUs. The NVUs are each configured for long-term tissue cultures (e.g., longer than 4 weeks). Each NVU includes a brain-specific microenvironment by integrating neural tissues and blood-brain-barrier (BBB) tissues. The BBB culture can be exposed to continuous, unidirectional fluid flow, mimicking in vivo physiology. Neural electrophysiology can be continuously monitored using integrated microelectrode array (MEA) biosensors. The cells and media from the platform can be harvested for multi-scale (phenotypic and -omics) data collection. The high-content data can be analyzed using computational MIDD algorithms. The MIDD processes are configured to identify molecular and dynamic changes and disease modifying targets for neurodegenerative diseases.

The NVUs can include a single tissue construct or an interconnected set of two-dimensional (2D) or three-dimensional (3D) cellular constructs that are frequently referred to as organs-on-chips, tissue chips, or in vitro organ constructs. The constructs are typically made with immortalized cell lines, primary cells from animals or humans, or organ-specific cells derived from naïve cells, human embryonic stem cells, and induced pluripotent stem cells (iPSCs). Individually, each construct can be designed to recapitulate the structure, function, and disease state of a human organ or organ region (e.g., portions of the brain), paying particular attention to the cellular microenvironment and cellular heterogeneity. When coupled together to create an MPS, these constructs offer the possibility of providing, in vitro, an unprecedented physiological accuracy for the study of cell-cell, drug-cell, drug-drug, and organ-drug interactions, if drug dynamics (e.g., drug interaction with tissue) can be properly modeled.

NVUs can provide numerous benefits to preclinical drug development. The use of microfluidic platforms can facilitate in vitro recreation of the mechanical, fluidic, spatial, and chemical stimuli and cues that a tissue may be exposed to in vivo. In some implementations, micro-machined biomimetic reactor platforms facilitate in vitro recreation of these stimuli. In many cases, single MPS and multiple MPS platforms can be designed to mimic specific organ functions, microarchitecture, and organ-organ crosstalk relevant to a biological question of interest. For example, the CIVMs (formed by the MPSs) are designed to mimic the in vivo tissue microenvironment by providing physiological cues. The cues can include flow rates that reproduce tissue-like perfusion and shear stress, tissue constructs composed of various human cell types, and so forth. The MPSs are configured to emulate phenotypic and molecular functions that are germane to preclinical drug discovery.

The system includes one or more NVUs to evaluate pharmacodynamics, pharmacokinetics, and safety pharmacology for neurodegenerative diseases. Each of the NVUs can include one or more MPSs, such as a brain MPS and a BBB MPS. The platform is configured to translate the results from the evaluation into a clinical trial design with quantitative systems pharmacology (QSP) and systems biology (SB) based in vitro to in vivo translation (IVIVT) algorithms. Pharmacodynamic studies with iPSC-derived PD MPS including four PD phenotypes will be designed for greater understanding of PD progression and the effects of therapeutic interventions. The system determines differences in PD phenotypes and their responses with several approved treatments to provide insights for PD precision medicine. Pharmacokinetic studies with iPSC-derived liver, gut, and BBB MPS will provide human-relevant clinical trial design parameters for FIH starting dose calculations. Safety pharmacology studies will help to estimate no observed adverse effect levels (NOAEL). The system is configured to process this multi-scale data from pharmacodynamic, pharmacokinetic and safety pharmacology studies to estimate first-in-human (FIH) doses. This comprehensive framework is a step towards clinical trial design without the use of animal models. Additionally, the system's SB-based machine learning algorithms provide mechanistic insights about the disease progression.

The platform can enable one or more technical advantages. The platform is configured to reduce preclinical discovery timelines for neuroscience. The platform facilitates drug discovery by capturing multi-cellular complexity and long-term progression of neurodegenerative diseases at a molecular kinetic scale. The platform can enable identification of novel drug pathways/targets and combination therapies more quickly and with less expense and health risks to patients than available methods. The results are improved from what can be obtained from human studies, diagnostic biomarker discovery for each PD phenotype, and mechanisms of action of pharmacology and safety pharmacology.

The one or more advantages described can be enabled by one or more aspects or embodiments of the platform. In an embodiment, a microphysiological system (MPS) includes at least one first inlet for receiving a fluid medium, a brain module comprising brain tissue, a blood-brain-barrier (BBB) module comprising BBB tissue, the BBB module configured to receive the fluid medium; and a crosstalk channel between the brain module and the BBB module, the crosstalk channel configured to promote a bidirectional crosstalk between the brain tissue and the BBB tissue in response to receiving the fluid medium at the BBB module.

In some implementations, the crosstalk channel comprises neuron-glia and glia-BBB crosstalk. In some implementations, the brain module comprises a plurality of compartments, the plurality of compartments comprising a neuron culture well and a glia culture chamber.

In some implementations, the brain tissue, the BBB tissue, or both the brain tissue and the BBB tissue are diseased with a neurodegenerative disease. In some implementations, the neurodegenerative disease is recreated from one of dopaminergic neurons or medium spiny neurons, astrocytes, pericytes, endothelial cells, microglia, oligodendrocytes, or a combination thereof. In some implementations, the neurodegenerative disease represents Parkinson's disease. In some implementations, the neurodegenerative disease is induced using one or more of a neurotoxin and a dopamine depletion treatment. In some implementations, the neurodegenerative disease is introduced using tissue comprising one or more disease genotypes.

In some implementations, the brain tissue of the brain module comprises one or more of human iPSC-derived neurons, microglia, and astrocytes. In some implementations, the BBB tissue of the BBB module comprises one or more of human brain microvascular endothelial cells (HBMECs), pericytes, and astrocytes.

In an embodiment, the MPS includes a microelectrode array (MEA) comprising one or more electrodes, the MEA being configured to perform an electrophysiology measurement comprising one or more of a network bursting frequency, an interburst interval, a burst duration, one or more neuron spikes, a per burst Ca2+ signaling, and a disease-relevant ion channel activity.

In an embodiment, the MPS includes a sensor configured to measure one or more biomarkers from the fluid medium, the biomarkers including one or more of neuroinflammation biomarkers, antioxidant molecules, oxidative stress biomarkers, or reactive oxygen species biomarkers.

In some implementations, the BBB module comprises a first medium channel and a second medium channel for receiving the fluid medium, and wherein the BBB tissue is in a BBB culture channel between the first medium channel and the second medium channel.

In an embodiment, the MPS includes a first outlet for sampling the fluid medium from the BBB module, a second outlet for sampling a second fluid medium from the brain module, or both the first and second outlets.

In a general aspect, a process includes obtaining, from a microphysiological system (MPS) comprising a brain module and a blood brain barrier (BBB) module, transcriptomics data for gene expression for a healthy phenotype and for a disease phenotype. The process includes training, based on the transcriptomics data, a machine learning model configured classify the healthy phenotype and the disease phenotype. The process includes determining one or more therapeutic targets for treatment of a neurodegenerative disease based on the machine learning model.

In some implementations, the process includes rank-ordering the one or more therapeutic targets based on one or more of, for each therapeutic target, a druggability, therapeutic evidence from a third party data source, a tissue specificity, safety or toxicity information, and a novelty.

In some implementations, the process includes simulating target perturbations. The process includes evaluating one or more of the therapeutic targets using the machine learning model.

In a general aspect, a process includes obtaining a microphysiological system (MPS) comprising brain tissue and blood brain barrier (BBB) tissue, wherein at least one of the brain tissue and the BBB tissue comprises a disease. The process includes treating the brain tissue and the BBB tissue with a drug or a combination of drugs to determine a phenotypic effect and a transcriptomic effect of the drug.

In some implementations, the process includes determining one or more phenotypic markers related to the disease. The process includes perturbing the brain tissue and the BBB tissue using the drug. The process includes optimizing at least one kinetic parameter representing the brain tissue or the BBB tissue. The process includes relating the perturbation to the phenotypic effect and the transcriptomic effect based on the optimization.

In some implementations, the process includes determining one or more therapeutic targets for treatment of a neurodegenerative disease based on context-specific genome-scale metabolic model (GEM). In some implementations, the process includes generating the GEM by: determining a tissue type represented in the MPS, preserving a gene-protein-reaction association based on tissue-specificity data, and performing a metabolic simulation including the gene-protein-reaction association to validate the GEM.

In some implementations, the one or more therapeutic targets comprise one or more of an mRNA, a protein, and a metabolite.

The details of one or more embodiments of these systems and methods are set forth in the accompanying drawings and the description to be presented. Other features, objects, and advantages of these systems and methods will be apparent from the description and drawings, and from the claims.

DETAILED DESCRIPTION

Figure 1:
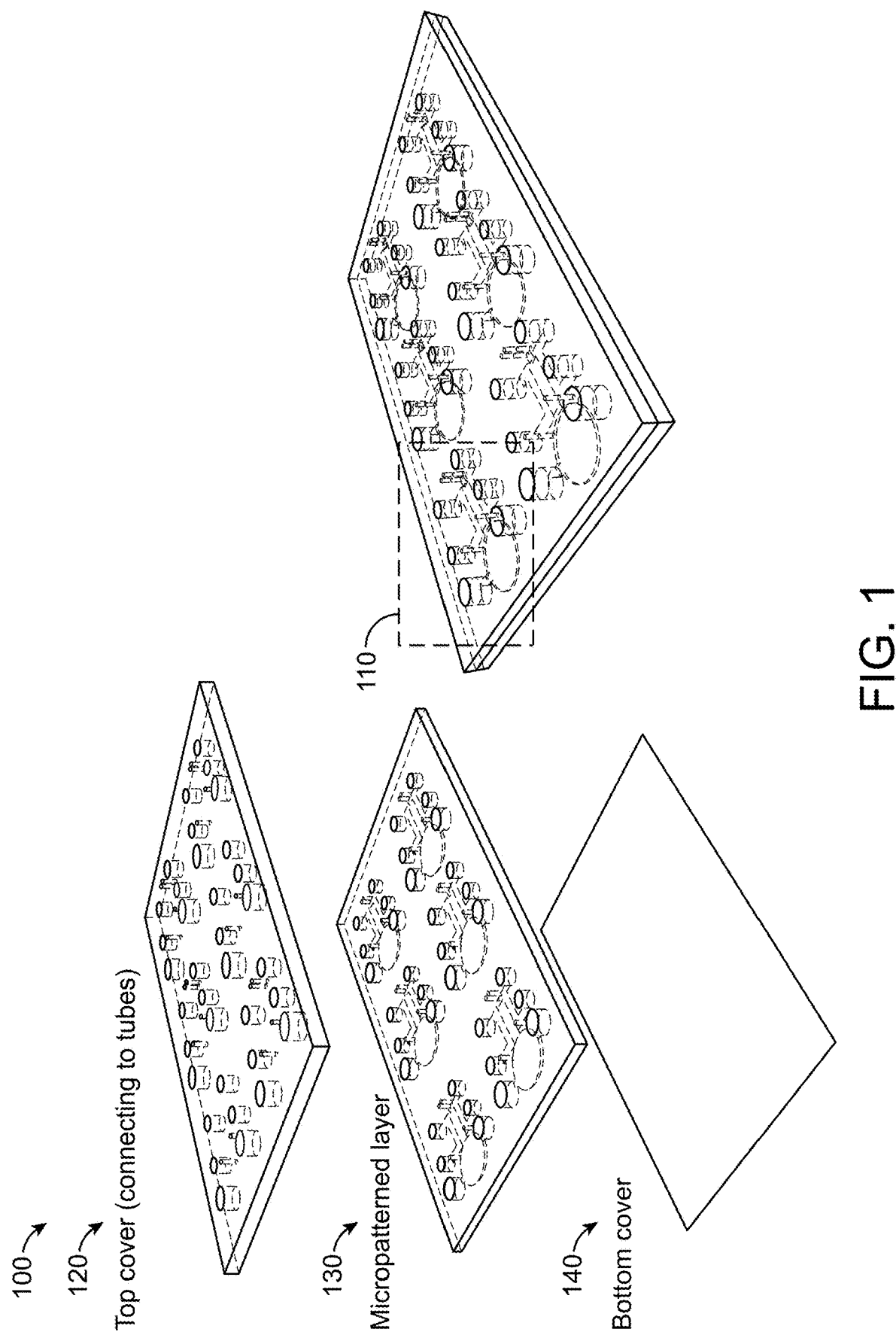
FIGS. 1-8 are diagrams illustrating example MPS platforms for preclinical drug discovery system for developing treatments (e.g., drugs) for neurodegenerative diseases.
Figure 6:
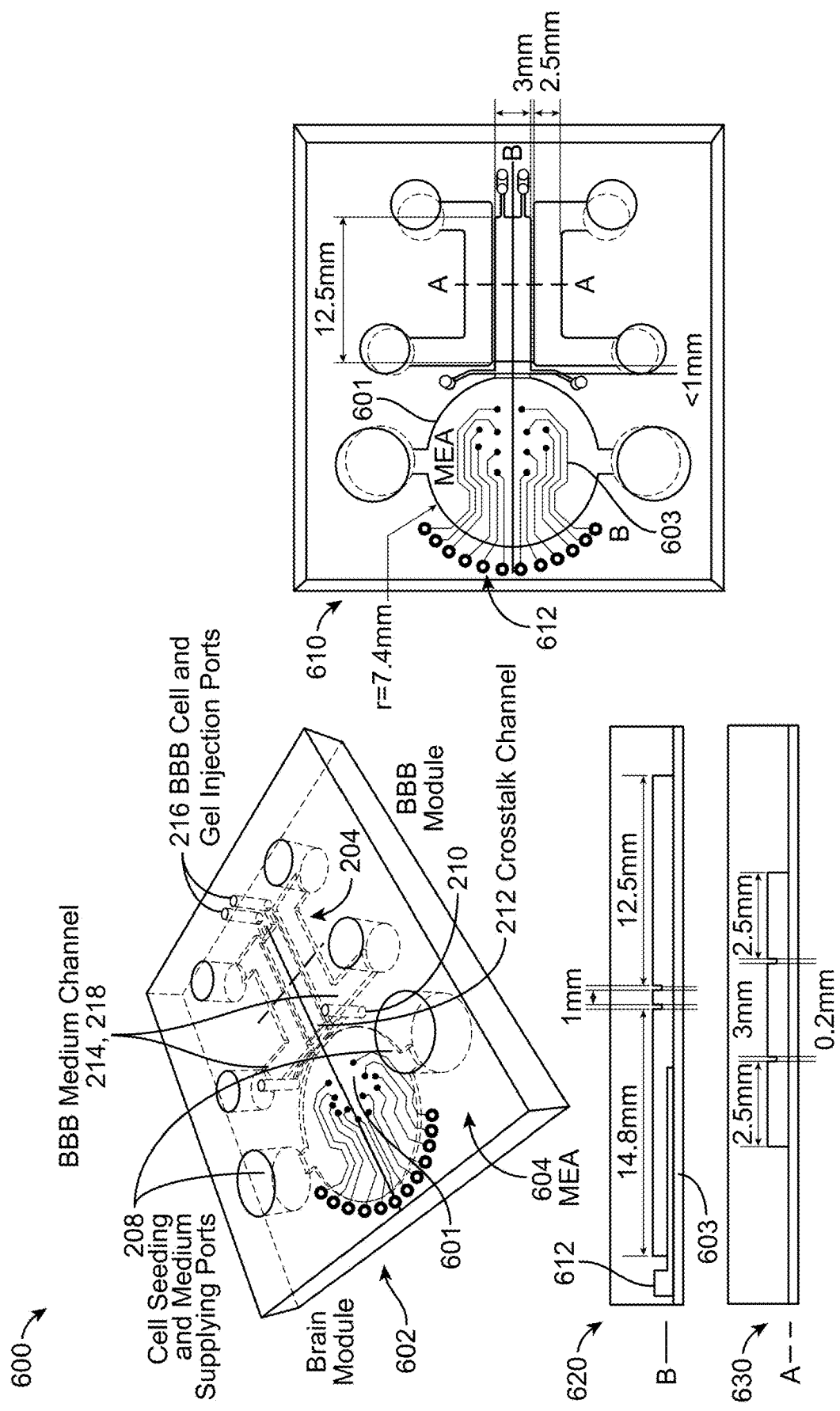

This disclosure describes a preclinical drug discovery system for developing treatments (e.g., drugs) for neurodegenerative diseases. FIG. 1 is a block diagram illustrating an example hardware platform 100 for hosting one or more neurovascular units (NVUs) 110. Each of the NVUs 110 is configured to enable preclinical drug discovery and assist in developing treatments for neurodegenerative diseases. Each of these NVUs 110 can include one or more microphysiological systems (MPSs), as subsequently described. Each of the NVUs enables long-term tissue mono-& co-culture (e.g., longer than 4 weeks). The NVUs 110 generally include a brain MPS representing a given brain region from a set of one or more brain regions of interest. The NVUs 110 generally include a blood-brain-barrier (BBB) MPS. The NVUs 110 generally include an interconnected BBB-brain MPS. The NVUs 110 can include one or more integrated microelectrode array (MEA) sensors (e.g., as shown in FIG. 6).

The NVUs 110 are configured for disease modeling by enabling emulation of tissues in controlled environments. The NVUs are configured to include BBB-brain tissue cultures. For performing a test, there can be an induction of disease in the NVU, hosted by the prepared tissues. The disease progression can be monitored over long periods of time. In some implementations, the NVUs can include cells from diseased patients. Many different mechanisms can be used for on-chip disease induction, as subsequently described.

The NVUs 110 are configured for disease characterization. For example, multi-scale assays can be performed using the NVUs 110. The NVUs 110 enable evaluation of cell construct and tissue construct functions. The NVUs 110 enable the system to compare healthy phenotypes and disease phenotypes. The NVUs 110 enable acquisition of data from targeted (phenotypic) metrics and untargeted (-omics) metrics, as subsequently described.

A computing system (not shown) uses data developed from the NVU 110 to combine human complex in vitro models (CIVM) with model-informed drug discovery (MIDD) methodologies in a processing workflow. The processing workflow, subsequently described in relation to FIGS. 9-13, can be used to develop an understanding of Parkinson's Disease (PD) pathophysiology and diagnostic and response biomarkers. The computational modeling is performed for target (e.g., drugs or drug combinations) discovery using the MPS data of the NVUs 110 and SB and quantitative systems pharmacology (QSP) based models. These models are configured to identify molecular abnormalities for diseased cells or tissues. The models link the molecular data to the phenotypic data. Here, phenotypic data can include clinical information regarding disease symptoms, as well as relevant demographic data (if applicable), such as age, ethnicity and sex.

The NVU 110 is configured to emulate portions of the brain. Data obtained from this emulation is used by the computing system model to validate a physiological relevance and identify molecular changes of various PD phenotypes. For example, the NVU 110 can be configured to identify and validate cell-specific targets for PD. The NVU can include a plurality of (e.g., at least two) MPSs, which are referred to as organ constructs and organ-on-chips (OOC). The MPSs of the NVU 110 are in fluid communication with one another. In some implementations, the MPSs are called compartments.

The NVU 110 includes physiologically relevant neurovascular MPS (e.g., brain and BBB modules subsequently described) for Parkinson's disease applications. The NVU 110 can include neurons, glial cells, endothelial cells, pericytes, and the supporting extracellular matrix. The NVU represents an important role in brain health, neurodegenerative disease, and pharmacology. The NVU 110 includes human iPSC-derived cells to develop stable tissue (e.g., greater than 28 days old) MPSs that mimic brain-specific cytoarchitecture and intercellular signaling microenvironments provides a platform to study neurodegenerative disease progression and pharmacology. For example, for a given stimulus (e.g., proinflammatory stimulation), a response can be observed. For example, changes in brain and BBB physiology mediated by neuron-glia and glia-BBB crosstalk could be a result of the given stimulus.

The NVU 110 is used to establish the striatal and (Substantia Nigra pars compacta) SNpc MPSs. The NVU 110 can include a brain module composed of human iPSC-derived neurons, microglia, and astrocytes. The NVU 110 can include a BBB module composed of human brain microvascular endothelial cells (HBMECs), pericytes, and astrocytes. The NVU's 110 cytoarchitecture supports the bidirectional neuron-glia and glia-BBB crosstalk known to play a role in health and disease including diseases with a proinflammatory component including Parkinson's and Alzheimer's. The brain MPS and the BBB MPS are described in greater detail in relation to FIG. 2.

The hardware platform 100 can be configured as follows. The platform 100 can include a top cover 120, a micropatterned microfluidic layer 130, and a bottom cover 140. The bottom cover 140 forms a base for the MPSs of the NVU 110. The bottom cover 140 supports the various chambers and channels of the MPSs of the microfluidic layer 130. The bottom cover 140 is a solid platform that stabilizes the MPSs and that provides a foundation for the MPSs.

The microfluidic layer 130 includes the chambers and channels of the MPSs for fluid flow through the system. The cells and tissues are hosted in these chambers and/or channels as needed to emulate organ functionality. The microfluidic layer 130 is patterned into a polymer material (e.g., a thermoplastic) as subsequently described. The microfluidic layer 130 is sandwiched between the bottom cover 140 and the top cover 120. The chip enables mono-cultures and co-cultures of various cell types in 2D and 3D. The cell source can be human primary cells, stem cells, or cell lines. For example, diseases can be modeled by differentiating from stem cells from patients to the relevant cell/tissue type for including in one or more MPSs of the multi-MPS platform 100. Alternatively, primary cells and/or immortalized cell line be used as sources for tissue in the MPSs. Generally, a stem-cell line is distinctly different from an immortalized cell line. Generally, primary cells are cells that have been isolated and then used relatively quickly (e.g., immediately). In some implementations, tissue including various genetic diseases can also be obtained using stem cell differentiations. Types of diseased cells can include (but are not restricted to) [DA neurons, astrocytes, microglia, and brain microvascular endothelial cells (BMEC)]. Neurodegenerative diseased tissue can be recreated from neurons (dopaminergic, medium spiny etc.), astrocytes, pericytes, endothelial cells, microglia, oligodendrocytes and so forth. Diseases can include inflammatory/immune diseases obtained from circulating immune cells, and T-cells. Any of these diseases can be hosted in the NVU 110.

The top cover includes interconnecting tubes for each of the MPSs of the NVU 110. In an example, the tubes of the top cover 120 connect one MPS to another MPS for perfusion. The tubes enable fluid flow at the desired rate so that organ functionality is accurately emulated.

Generally, the top cover 120, the bottom cover 140, and the microfluidic layer of the NVU 110 and the MPSs included in the NVU are fabricated into thermoplastic materials. The fabrication can include one or more processes such as laser/plotter cutting, CNC machining, and microinjection molding. The NVU 110 can be fabricated using thermoplastics such as polymethyl methacrylate (PMMA), polycarbonate (PC), polysulfone (PSU), or cyclic olefin copolymer (COC). In some implementations, the hardware platform 100 is PDMS-free to minimize undesirable non-specific adsorption of lipophilic molecules. The bottom cover 140 can be laminated with a gas permeable material to accurately reflect the incubator conditions. While three layers are shown in FIG. 1, a fourth layer can be included. The fourth layer includes a membrane layer between the top cover 120 and the microfluidic layer 130.

Figure 2:
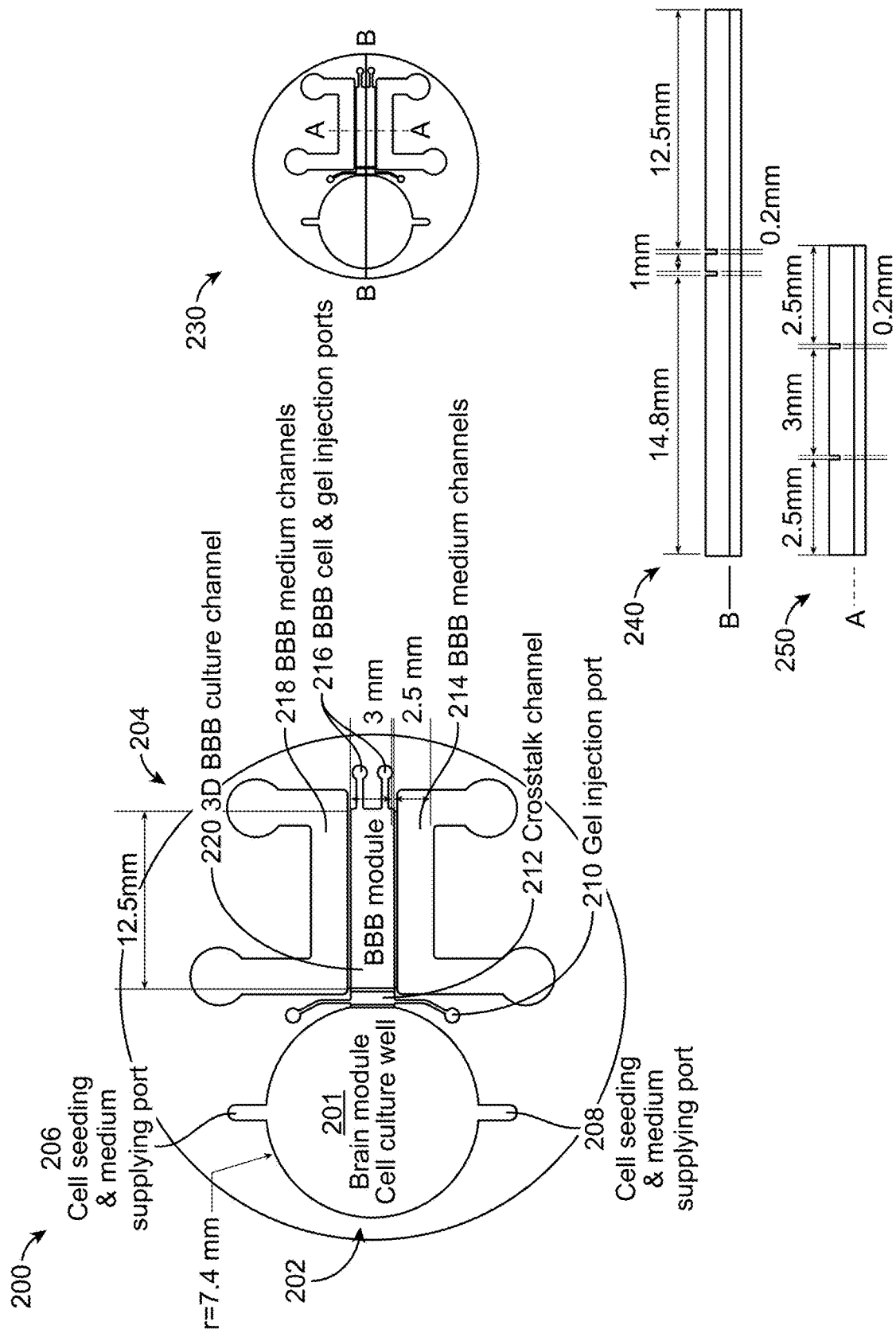
Figure 3:
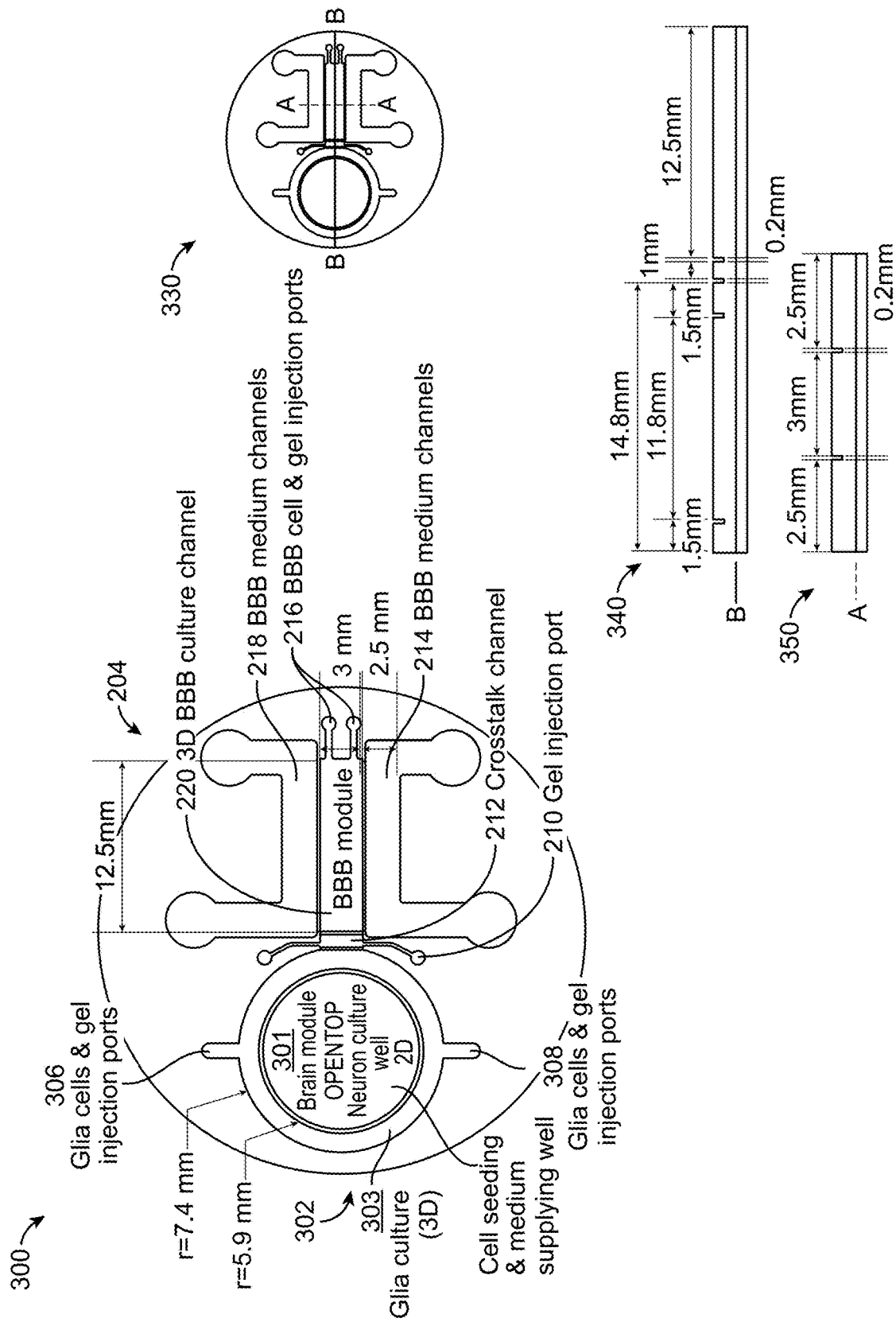

FIGS. 2 and 3 show examples of an NVU 200 and an NVU 300, respectively. NVU 110 for the hardware platform 100 of FIG. 1 can include either of NVU 200 or NVU 300. The NVU 200 includes a brain compartment 202 and a microvascular BBB compartment 204 connected by a crosstalk channel 212. View 230 is a top view of the NVU 200. View 240 is a side view of the NVU 200 along axis B shown in view 230. View 250 is an edge view of NVU 200 along axis A shown in view 230.

The brain module 202 includes of a main chamber 201 that includes the cells or tissue of interest. The brain module 202 includes two side ports 206, 208 for cell seeding and media changes for the brain module. Generally, the brain module 202 is configured to culture brain cells, such as neurons, microglia, astrocytes etc. The brain module 202 can recapitulate the physiology from various brain regions using certain cell types, such as dopaminergic neurons for substantia nigra pars compacta, or medium spiny neurons for stratum. The brain module 202 can be static or perfused. In the example of FIG. 2, the brain module 202 has a radius of 7.4 millimeters (mm). However, this size can be scaled up or down from this value. In some implementations, the brain module chamber 201 is about 14.8 mm long, as shown in side view 240 in FIG. 2 along axis B.

The BBB module 204 includes three channels. The channels include a center channel 220 for the three-dimensional (3D) BBB microvasculature culture. The channels include two side channels 214, 218 for a medium support and two ports 216 for injection of mixture of cells and gel. The flow through the BBB 204 occurs from one fluidic channel 214 to the other 218 or vice versa. The blood-brain-barrier (BBB) module 204 is configured to culture BBB cells, such as human brain microvascular endothelial cells (HBMEC), pericytes and astrocytes. The BBB module 204 is generally perfused for HBMEC to construct vascular network in the BBB module. The BBB module 204 center channel 220 can be approximately 3 mm in width. The two side channels 214, 218 can be about 2.5 mm in width. The length of the BBB module 204 center channel can be about 12.5 mm. However, these values can each be scaled up or down as needed.

The crosstalk channel 212 connects the BBB module 204 and the brain modules 202. In some implementations, the crosstalk channel 212 has two gel injection ports 210. In some implementations, the cross-talk channel 212 can be about 1 mm long. All gel channels have the leak-preventing guides to prevent gel leakage into other channels. Gel leakage is prevented due to surface tension with the leak-preventing guides. Further dimensions of the membrane and areas between the channels are shown in views 240, 250. For example, there is a leak-preventing guide of about 0.2 mm between the crosstalk channel 212 and each of the brain module 202 chamber 201 and the BBB module 204 channel 220. These values are exemplary and can be scaled up or down.

Both compartments 202, 204 of the NVU 200 support physiologically relevant cytoarchitecture and contain access ports 206, 208 and channels 214, 218 for medium changes, sampling, and drug dosing. The BBB compartment 204 is perfused to support physiological BBB maturation and drug transport experiments. The crosstalk channel 212 facilitates the exchange of nutrients, signaling molecules, and drugs between the brain compartment 202 and the BBB compartment 204. A sterilization process uses one or more of several approaches such as autoclave, supercritical $CO_2$, gamma irradiation, ethylene oxide (EtO), and isopropyl alcohol, depending on a selected device material.

Generally, computational fluid dynamics (CFD) modeling is used to design the medium channels of the BBB module 204 based on the computational flow characteristics. A modeling engine, such as COMSOL Multiphysics®, can be used to simulate a concentration gradient and distribution of molecules secreted from cells or molecules/drugs introduced in the system. The NVU 200 is characterized based on biocompatibility and suitability for long term culture (e.g., greater than 28 days). The biocompatibility and suitability can be validated by cell viability and cytotoxicity assays. To characterize the diffusion properties of molecules through the crosstalk channel, various sizes of fluorescent dextran are introduced into one or both modules and visualized by confocal or epi-fluorescent microscopy. In some implementations, the brain compartment 202 is established in a microelectrode array (MEA) platform (e.g., a 24-well headstage with an interface board and data acquisition software). In an example, the MEA platform (not shown) can be used for analysis of, and perturbations to, a neuron-glia crosstalk's influence on neuronal electrical activity under healthy and PD conditions. The MEA can be integrated into the NVU 200 design, supporting the real-time evaluation of the effects of BBB (patho-)physiology on neuronal activity.

FIG. 3 shows an example NVU 300 that is similar to NVU 200 of FIG. 2. The brain module 302 of NVU 300 of FIG. 3 includes a cell culture well 301 that is surrounded by a 3D cell culture channel 303. The 3D cell culture channel 303 includes gel injection ports 306, 308. Additionally, the cell culture well 301 in the brain module 302 can be open to the air, while the brain module 202 of FIG. 2 is generally covered by a top plate. View 330 is a top view of the NVU 300. View 340 is a side view of the NVU 300 along axis B shown in view 330. View 350 is an edge view of NVU 300 along axis A shown in view 330.

The dimensions shown in views 340, 350 are examples and can be scaled up or down as needed. The 3D cell culture channel 303 can be about 1.5 mm wide. The brain module 302 chamber 301 is about 11.8 mm in diameter. In other words, the chamber 301 can have a radius of about 5.9 mm, while the 3D cell culture channel 303 and chamber 301 together have a radius of 7.4 mm.

Figure 4:
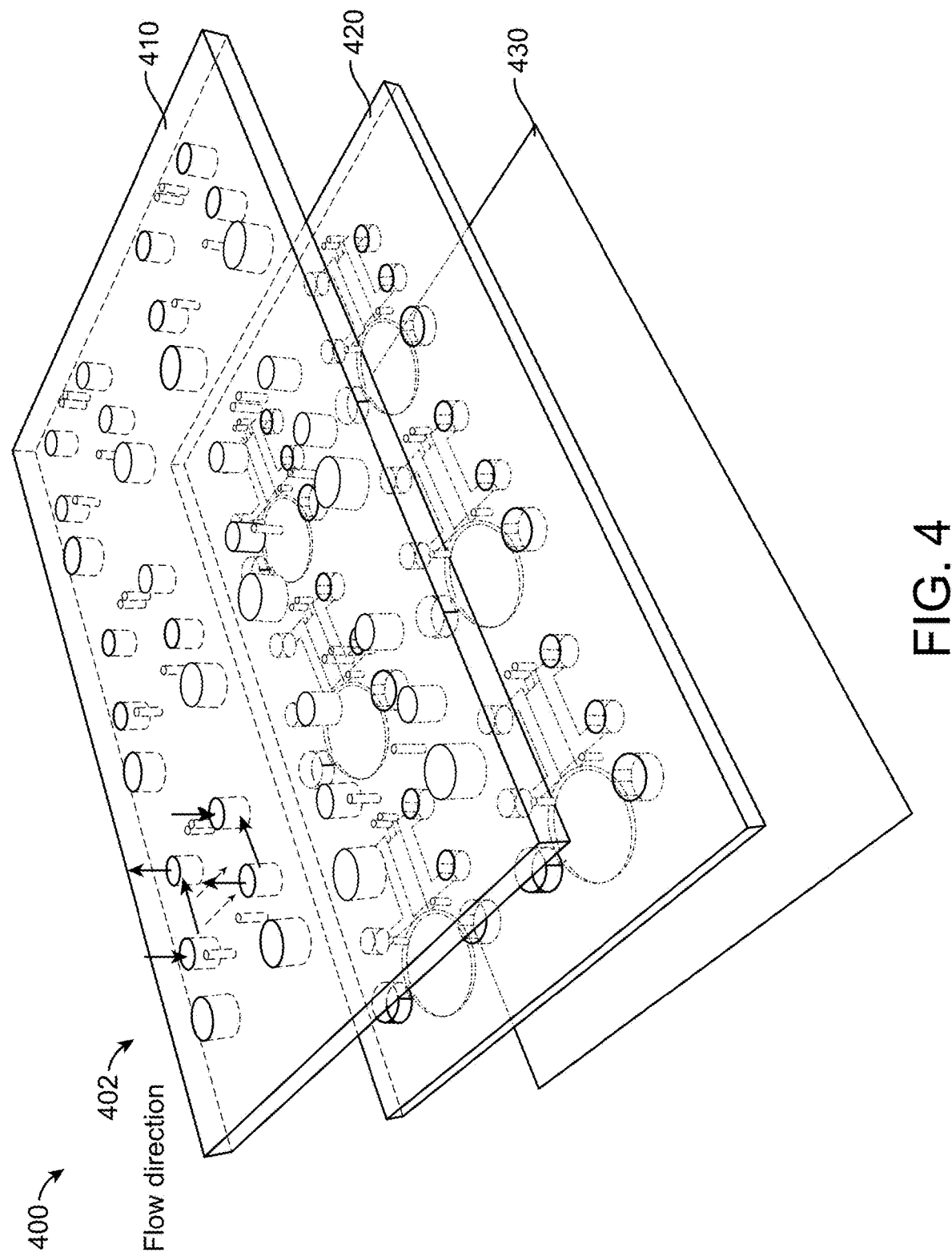
Figure 5:
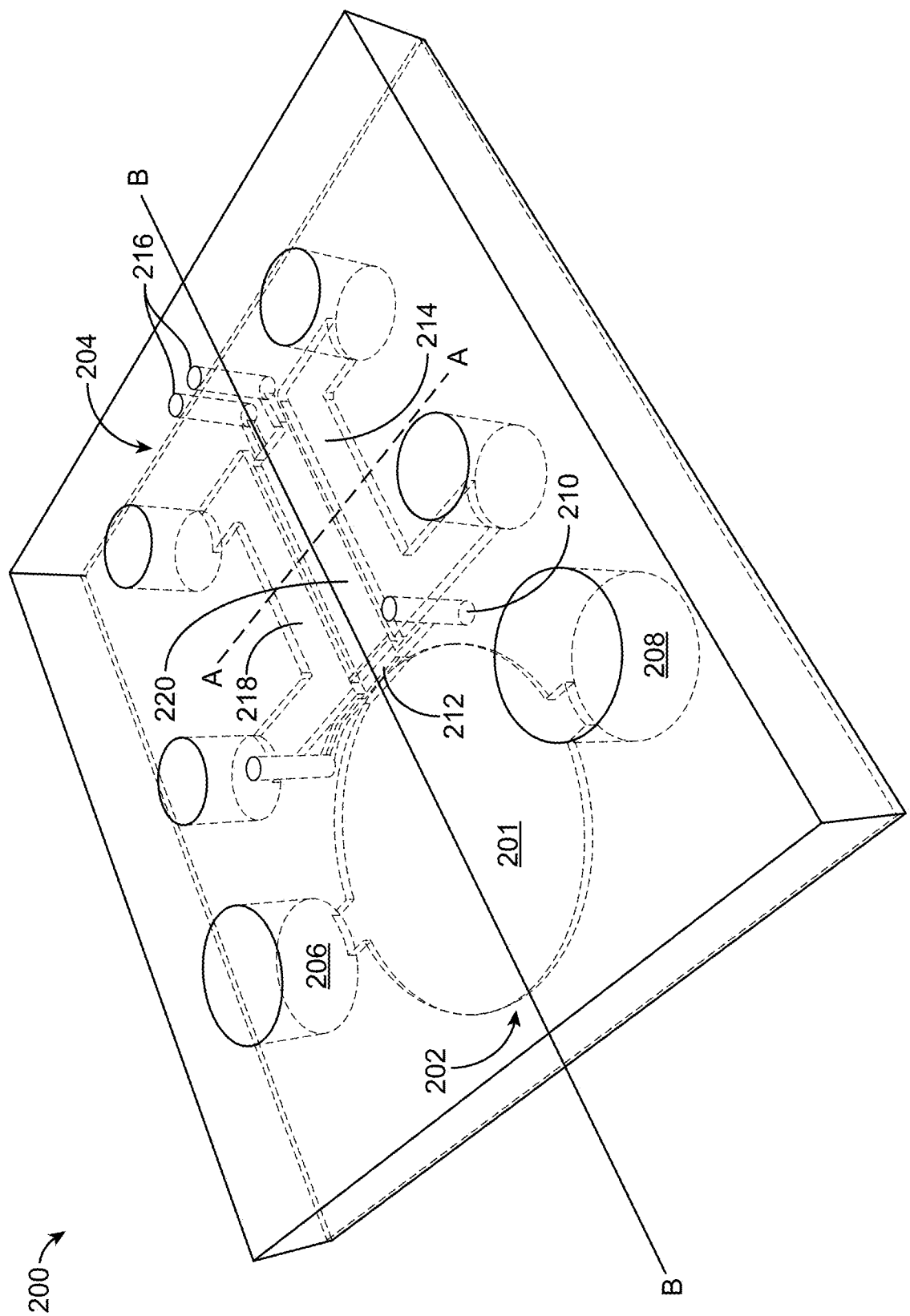

FIG. 4 shows a detailed exploded view of the layers of a hardware platform 400, which is similar to the hardware platform 100 of FIG. 1. In FIG. 4, an example flow direction 402 is shown for a particular NVU. The flow direction 402 is through the top cover 410. The medium can flow through the microfluidic layer 420, which includes the modules of NVUs 200, 300 described in relation to FIGS. 2-3. The flow direction 402 shows two flow directions along BBB medium channels (e.g., channels 214, 218 of FIGS. 2-3). FIG. 5 shows a 3D perspective view of the NVU 200 of FIG. 2.

FIG. 6 shows an example NVU 600 similar to NVUs 110, 200, 300 previously described. NVU 600 includes a brain module 602 including an MEA 604. View 610 is a top view of the NVU 600 showing traces 603 of the MEA 602. The traces 603 can connect to contacts such as contact 612 outside of the chamber 601. View 620 shows a side view along axis B of the NVU 600. A profile of the contact 612 and trace 603 of the MEA are shown. View 630 shows a front view along axis A of the NVU 600. Each of views 610, 620, and 630 are associated with example dimensions for the brain module 602 and BBB module 204. The MEA 604 can be used to measure cell activity (e.g., of neurons).

Figure 7:
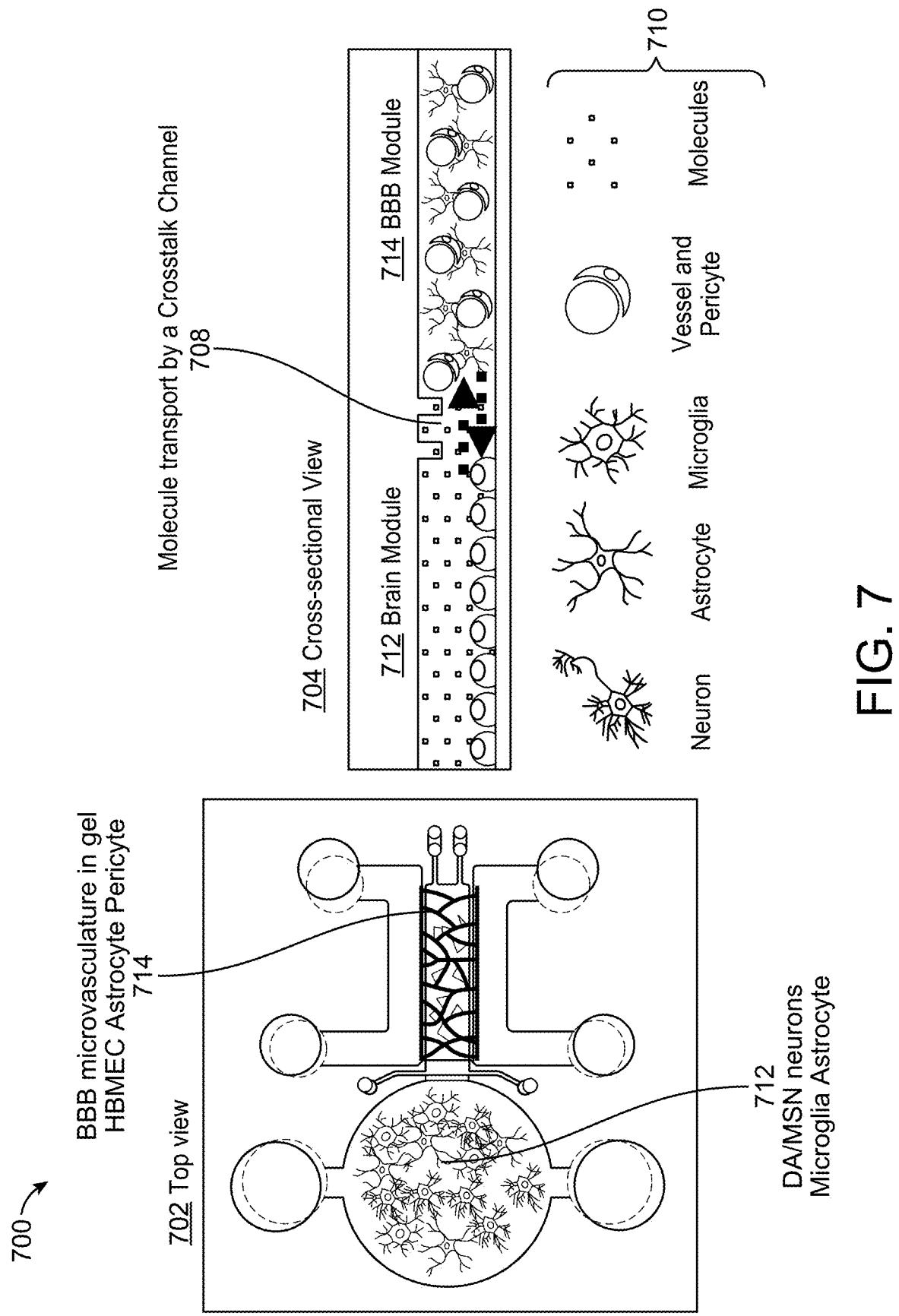

FIG. 7 shows an example NVU 700, similar to NVUs 110, 200, 300, and 600 previously described. Various cell types can be added to each compartment. For example, at least one tissue type can be included. The cell-type in the brain module 712 is based on which brain region is selected to be studied. For example, dopaminergic (DA) neurons are used for substantia nigra pars compacta. In another example, medium spiny neurons (MSN) are used for the stratum, and so forth. The cells may be added to each module at different time points. For example, neurons are generally added first, and then astrocytes and microglia. The tissue construct in brain compartment can be 2D (flat culture) or 3D (embedded in gel). After addition of the cell types, the tissues are cultured to build a dynamic microenvironment between each module.

The BBB module 714 may include of human BBB cells such as endothelial cells, pericytes and astrocytes. The vascular networks are formed by media perfusion through seeded HBMECs. The brain module 712 may include neurons, astrocytes, microglia, and oligodendrocytes. The brain culture can be static or perfused. Various cell types 710 can also be added as shown in the cross-sectional view 704. A top view 702 shows the brain module 712 including DA/MSN neurons, microglia, and astrocyte. The top view 702 shows the BBB module 714 including microvasculature in gel with HBMECs, astrocytes, and pericytes.

To evaluate the NVUs previously described, the BBB modules and brain modules can be individually evaluated prior to combining them into the NVU. This establishes physiologically relevant brain and BBB modules (MPSs). In an example, for neuron characterization, healthy iPSC-derived striatal MSNs (e.g., BrainXell BX-0700) are plated on ECM-coated substrates and evaluated over time (more than 14 days) for their expression of the relevant proteins DA- and cAMP-regulated neuronal phosphoprotein (DARPP-32), gamma aminobutyric acid (GABA), and microtubule-associated protein 2 (MAP2). Healthy iPSC-derived midbrain DA neurons (CDI R1108) and SNCA (A53T) mutant derived-iPSC DA neurons (CDI R1110) are plated on ECM-coated substrates and evaluated over time (e.g., more than 14 days) for their expression of the relevant transcription factors FoxA2 and Lmx1. The expression of tyrosine hydroxylase (TH), the enzyme responsible for converting tyrosine to L-3,4-dihydroxyphenylalanine (L-DOPA), is determined.

For glial cell characterization, iPSC-derived microglial cells (CDI R1131) are plated onto ECM-coated substrates and characterized for morphology and for their expression of CX3C chemokinereceptor (CX3CR1), transmembrane protein 119 (TMEM19), and ionized calcium binding adaptor molecule (Iba1) before and after activation by lipopolysaccharide (LPS 1 ng/mL). iPSC-derived astrocytes (CDI R1092) are plated onto ECM-coated substrates and characterized for morphology and for their expression of CX3CR1, GFAP, vimentin, and S100 calcium-binding protein R(S1000) before and after activation by LPS. For both glial cell types, media are reserved for PD relevant proinflammatory cytokine secretion analysis using the MesoScale Discovery (MSD) Neuroinflammation Panel 1 (NP1) (e.g. interleukin-6 (IL-6), tumor necrosis factor alpha (TNF-α), and interleukin 1 beta (IL-10)). In some implementations, oligodendrocytes can be incorporated in the brain module.

For the brain module MPS characterization, an MSN (striatal) and DA neuron (SNpc) brain modules are established by first plating iPSC-derived neurons on either the MCS 24-well plate or the NVU MPS device and then plating a glial cell-containing (iPSC-derived microglia and astrocytes) collagen-laminin-fibronectin gel topcoat. The initial ratio of astrocytes to microglia to neurons is approximately 2:1:1. This approach facilitates the evaluation of neuronal activity while providing the physiologically relevant cytoarchitecture to support neuron-glia crosstalk. The brain MPS is evaluated for Lewy body formation (ICC), ROS production, and neuronal oxidative stress (CellROX™, Invitrogen), and cytokine secretion.

For MEA recordings, the spontaneous and compound-modulated electrical activity of the MSNs and DA neurons are evaluated using the brain MPS established on MEAs (e.g., as shown in NVU 600 of FIG. 6). Spontaneous activity of the neurons is recorded using the MCS MEA platform 600. The data are analyzed using spike detection and sorting and time series analysis methods. Following a functional maturation period (e.g., 14 days), a baseline neuronal electrical activity is recorded. Next, systems are acutely treated (single dose) with a proinflammatory molecule (LPS 1 μg/mL). After 24 hrs, neuronal electrical activity is recorded and the media reserved to determine cytokine and ROS production (Promega ROS-GLO™). After all measurements are completed, oxidative stress (CellROX™, Invitrogen), glial cell activation (ICC), and cell viability (SYTOX Green, Invitrogen) are determined using a subset of systems. The brain MPSs is imaged using confocal or epi-fluorescent microscopy.

The BBB MPS is characterized as follows. The 3D perfusable BBB microvasculature is developed using a tri-culture of human brain microvascular endothelial cells (HBMECs) with pericytes and astrocytes in a fibrin hydrogel. A cell seeding density ratio of 6:1:1 HBMEC to pericytes to astrocyte can be used, but this ratio is can be adjusted as needed. After the BBB microvasculature forms, the system is characterized for the expression of tight junction proteins including zonula occludens-1 (ZO-1), occludin, claudin-5 and cell surface proteins such as P-glycoprotein (Pgp) using ICC in the presence or absence of LPS stimulation, BBB barrier integrity are functionally evaluated using an endpoint apparent permeability test by introducing fluorescent dextran molecules (4, 70, and 150 kDa) or drugs of interest into the positive pressure medium channel and calculating the flux of solute across the area of capillary wall within the tissue gel region after transport through the BBB microvessels. Subsequently, the perfused microvessels are imaged by confocal or epi-fluorescent microscopy. Using a mass conservation method, the amount of the fluorescent dextran passing through the microvessels over unit time is equal to the rate at which it accumulates outside of microvessels in the tissue gel region. An image analysis is conducted.

Physiologically relevant NVU MPSs (striatal and SNpc) are demonstrated evaluating the effects of a proinflammatory stimulus. Either MSNs (for striatal NVU) or DA neurons (for SNpc NVU) will be plated into the ECM-coated (collagen-laminin-fibronectin) brain compartment of the MPS device. Following a 24 hr equilibration period, a glial cell (microglia and astrocytes)-containing ECM hydrogel topcoat is plated, completing the 3D brain module. Concurrently, the perfusable BBB microvasculature module is established by employing a tri-culture of HBMECs with pericytes and astrocytes in a hydrogel. All individual cell types are established and cultured in their respective vendor recommended media formulations during seeding and recovery in the MPSs. After the recovery period, the cells are cultured using the CDI recommended serum-free brain neuron medium formulation (CDI M1010, M1031, and M1029).

Neuron-glial crosstalk occurs within the brain module and neuron-BBB crosstalk occurs across the central crosstalk channel of the MPS. After a maturation period (e.g., 14 days), the medium is sampled from the MPSs for cytokine concentration determination. Next, systems are acutely treated (e.g., with a single dose) with a proinflammatory molecule (LPS 1 μg/mL) in the BBB module. After 24 hours, neuronal electrical activity is recorded, and the media reserved to determine cytokine and ROS production. After all measurements are completed, endpoint assays are conducted. Phenotypic changes to the BBB are evaluated. The effects of the LPS treatment are compared to the untreated control NVU MPSs. An NVU MPS supporting cell viability up to 28 days and that responds physiologically to proinflammatory stimulation is considered robust.

Figure 8:
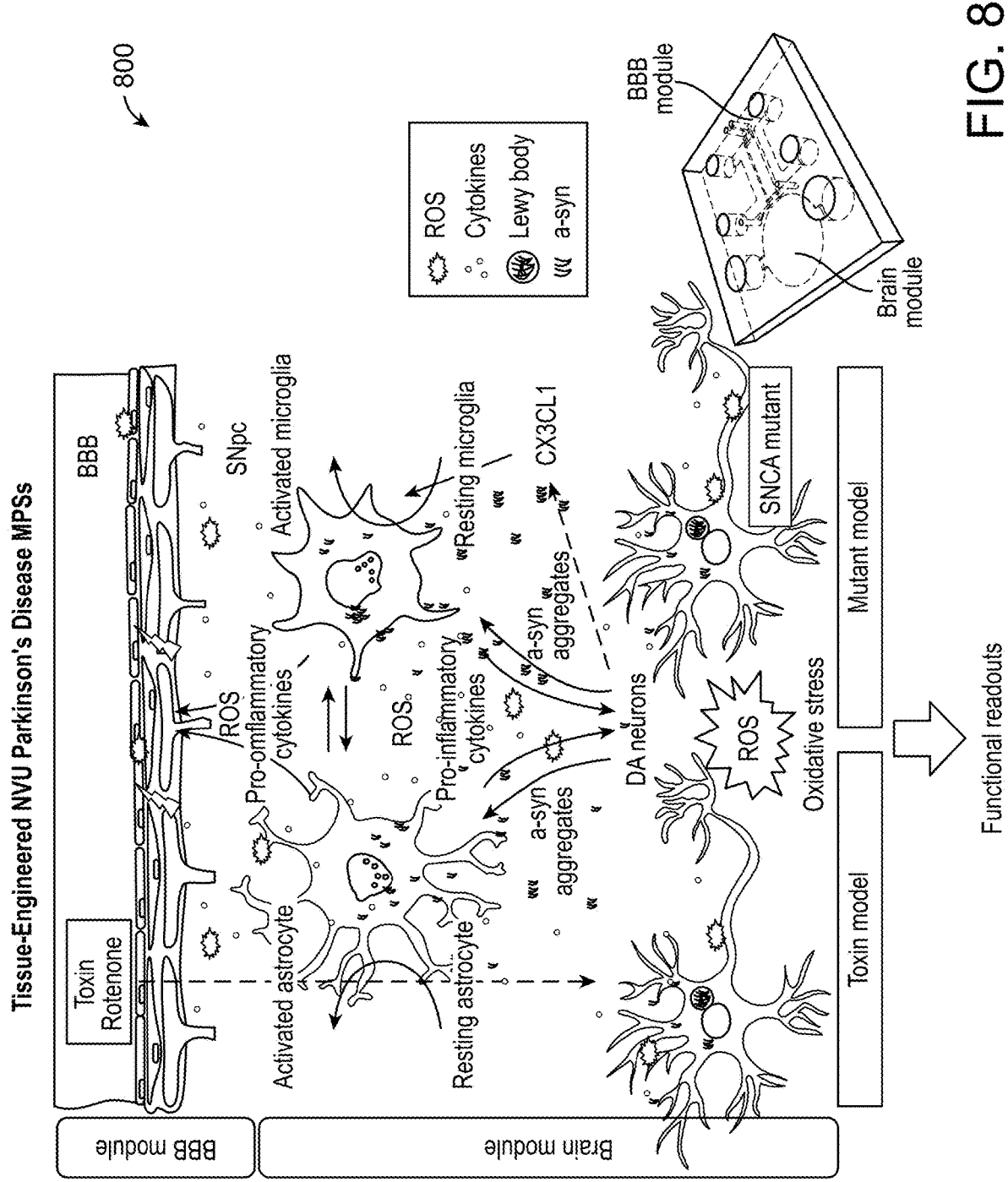

FIG. 8 illustrates an example NVU 800 representing a tissue-engineered approach to establish NVU Parkinson's Disease (PD) MPSs. As previously described, by combining the relevant brain (neurons, microglia, and astrocytes) and BBB (HBMECs, pericytes, and astrocytes) cytoarchitecture in a functional MPS, the clinically-observed phenotypic characteristics of PD and disease-relevant crosstalk can be evaluated using a single device, and therefore, be used to identify novel molecular changes of the disease.

A neurodegenerative disease (such as Parkinson's) can be induced on the NVU 800 in various ways. For example, on chip disease induction can be used. This includes using neurotoxin (rotenone) to reduce DA neuron function, or dopamine depletion for medium spiny neurons. In another example, cells with disease genotypes can be added to the MPSs, such as SNCA A53T mutant cells for Parkinson's disease. After disease induction, the system demonstrates various neurodegenerative disease phenotypes, such as astrocyte and microglia activation, a-synuclein accumulation, neuroinflammation, cytokine release, etc. The tissue culture continues after disease induction (e.g. 1+ week) to observe pathophysiological changes and determine the progression. These changes are observed throughout the disease progression studies and quantified with various assays. The assays can include neuron activity (function) with MEA, BBB integrity with FITC permeability assay, cytokines with ELISA, gene expression with transcriptomics, metabolites by metabolomics and proteins by proteomics, and so forth. The disease progression studies are simultaneously run with a contrasting "healthy—non diseased" condition to compare the molecular changes to a baseline.

To perform disease characterization (both phenotypic and -omics), one or more brain metrics can be observed. Data are gathered to track the metrics, and this data are combined with the machine learning models subsequently described. Generally, the brain metrics include electrophysiology data, biomarkers (e.g., intracellular & extracellular), gene expressions, and -omics data. Examples of these metrics are included below, and how these metrics are used in computational models is subsequently described in relation to FIGS. 9-13.

Brain metrics can be obtained from electrophysiology measurements. For electrophysiology-based brain metrics, the following can be measured. The metrics include a neuron firing frequency (e.g., action potentials), a time to half-peak width, and identification of neuronal subpopulations. Neural network formation and activity based metrics can be measured, including synaptic connectivity and plasticity. The metrics include network bursting frequency, interburst interval, burst duration, neuron spikes (e.g., action potentials) and per burst $Ca^{2+}$ signaling by $Ca^{2+}$ imaging. The measurements can include interrogation of disease-relevant ion channel activity and dysfunction using agonists and antagonists, including metabotropic glutamate receptors (mGluRs) and ATP-sensitive potassium channels (KATP channel). The measurements can include interrogation of disease relevant neurotransmission including evaluating the roles of acetylcholine (ACh) signaling in a DA neuron chip, GABAergic signaling in a MSN chip, dopamine (DA) signaling in the MSN chip, and glutamate-mediated excitotoxicity in a MSN chip. The measurements can include astrocyte-dependent alterations in DA neuron (e.g., for the DA neuron chip) and MSN (e.g., for the MSN chip) signaling and network activity.

The metrics can include secreted biomarkers (e.g., measured by a biomarker sensing apparatus). For example, for neuroinflammation, biomarkers include cytokines: interferon gamma, tumor necrosis factor alpha, interleukin-1 beta, interleukin-6, and interleukin-8. Biomarkers can include reactive oxygen species (ROS) such as superoxide ions, peroxides, and hydroxyls. Biomarkers can include reactive nitrogen species (RNS) such as nitric oxide. Biomarkers can include antioxidant molecules such as catalase (CAT), superoxide dismutase (SOD), and glutathione peroxidase. Biomarkers can include oxidative stress gene expression in microglia (e.g., NADPH oxidase).

Brain metrics can include gene expression based metrics. Gene expression can include (RT-qPCR), such as tyrosine hydroxylase (TH), aromatic amino acid decarboxylase (AAAD), monoamine oxidase (MAO), catechol-O-methyl transferase (COMT), aldehyde dehydrogenase (ALDH), and GTP cyclohydrolase (GTPCH).

Brain metrics can be based on cell morphology for disease status. For example, immunocytochemistry (ICC) for tyrosine hydroxylase (TH) can be measured. In other examples, alpha-synuclein aggregate formation/deposition (Lewy bodies) by ICC is measured. In some implementations, TH and phospho-TH concentration by ICC or ELISA are measured. Other proteins to measure can include: DJ-1 (PARK7) and leucine-rich repeat kinase 2 (LRRK2). A synaptic protein expression by ICC or gene expression can be tracked, such as dendritic spine structure and remodeling. In some implementations, synaptic protein expression by ICC or gene expression are tracked, such as dopamine receptors (D1-D5).

Several example experiments to validate the NVUs for PD analysis are now described. In an aspect, the NVU 800 is characterized by establishing a striatal (MSN) NVU PD MPS and characterizing the pathophysiological relevance with phenotypic and transcriptomic profiles. The effects of DA withdrawal during MSN recovery/maturation on excitatory glutamate stimulation are evaluated. DA signaling modulates dendritic spine density in MSNs. Withdrawal of DA signaling, as occurs in PD, results in a reduction in dopamine receptor (D1R and D2R) expression causing hyperexcitability in response to glutamatergic synaptic input. Experimentally, DA treatment facilitates dendritic spine formation in cultured MSNs through D1R and D2R signaling. To mimic the healthy condition, the brain and BBB MPSs of NVU 800 are treated with DA during daily medium changes to facilitate MSN dendritic spine maturation. The NVU 800 MPSs are established by combining the MSN-brain with microvascular BBB modules previously described in relation to FIGS. 2-7.

During the maturation process (e.g., about 14 days), systems are treated with DA during medium changes (e.g., healthy) or not treated (e.g., diseased). The brain module is independently established, such as in the MEA NVU 600. Following the functional maturation period of the diseased and healthy systems, baseline neuronal electrical activity is recorded, and media reserved to determine oxidative stress, cytokine, and ROS production. Next, systems are treated with an excitatory neurotransmitter, glutamate, and neuronal activity recorded. After the period of maximal neuronal dysfunction (hyperexcitability) is observed with the MEA, neuron electrical activity is imaged using $Ca^{2+}$ imaging to evaluate neuronal function in the NVU 800 MPS. Cells in the brain and BBB modules of the healthy and diseased NVU 800 MPS are harvested for transcriptomic analysis. Culture media are reserved from disease and healthy control NVU MPSs to determine cytokine and ROS production.

After all measurements are completed, endpoint assays are conducted as previously described. Phenotypic changes to the BBB are conducted as previously. A striatal PD NVU MPS that exhibits MSN hyperexcitability in response to glutamate stimulation is considered sufficient for further modeling.

In an aspect, a genetic mutant (SNCA A53T DA neuron) SNpc NVU PD MPS is established. The pathophysiological relevance is characterized with phenotypic and transcriptomic profiles. The A53T SNCA gene mutant is selected for the evaluation because these mutant DA neurons exhibit α-synuclein pathology and accumulate intracellular Lewy bodies, a hallmark of the PD phenotype. DA neuron (A53T mutants or isogenic controls) containing brain and BBB modules are seeded to establish the NVU 800 MPS. Following a functional maturation period (e.g., about 14 days) media are reserved to determine oxidative stress, cytokine, and ROS production.

The brain module is independently established in the MEA NVU 600 device previously described. The electrical activity of the mutant and isogenic DA neurons is repeatedly evaluated for a period of up to 14 days to determine the window of maximal dysfunction in mutant systems compared to isogenic control systems. After the period of maximal neuronal dysfunction (determined using MEA), neuron electrical activity is imaged using $Ca^{2+}$. The cells in the brain and BBB modules of the NVU MPS are harvested for transcriptomic analysis. Culture media are reserved from disease and healthy control NVU MPSs to determine cytokine and ROS production.

After all measurements are completed, endpoint assays are conducted as previously described. Phenotypic changes to the BBB are conducted. An SNCA (A53T) SNpc PD NVU MPS that exhibits DA neuron Lewy body formation and reduced spontaneous neuronal activity and glial cell activation is considered sufficient to proceed to further modeling.

In a general aspect, a toxin-induced (rotenone) SNpc NVU 800 PD MPS is established. The pathophysiological relevance of the NVU 800 is characterized with phenotypic and transcriptomic profiles. Rotenone can be selected for the evaluation because DA neurons exhibit α-synuclein pathology and accumulate intracellular Lewy bodies, a hallmark of the PD phenotype. DA neuron containing brain and BBB modules are seeded as previously described to establish the NVU 800 MPS. The brain module is independently established in the MEA NVU 600.

Following a functional maturation period (e.g., 14 days), media are reserved to determine oxidative stress, cytokine, and ROS production. Next, systems are treated with rotenone (50 nM) for 48 hrs to induce a PD-like phenotype. Following a full medium change to dilute the toxin in the systems, neuronal activity is recorded. The neuron electrical activity of the brain-MEA is monitored for up to 2 weeks. After the period of maximal neuronal dysfunction (determined using MEA) neuron electrical activity in the NVU MPS is determined using $Ca^{2+}$ imaging. The cells in the brain and BBB modules of the NVU MPS are harvested for transcriptomic analysis. Finally, spent culture media are reserved from disease and healthy control MPSs to determine cytokine and ROS production.

After all measurements are completed, endpoint assays are conducted as previously described. Phenotypic changes to the BBB are conducted. This validates transcriptomic profiling for the toxin-induced NVU PD MPSs. A rotenone SNpc PD NVU MPS that exhibits DA neuron Lewy body formation and reduced spontaneous neuronal activity and glial cell activation is considered sufficient for additional modeling.

In addition to PD, other neurodegenerative diseases can be studied in the platform 100. For example, for Alzheimer's disease, brain metrics can be observed using hippocampal neurons or cortical neurons. The disease is induced using amyloid-beta 42 oligomers or tau oligomers. In another example, a amyloid precursor protein (APP gene mutation) model in hippocampal or cortical neurons can be used.

Treatments for Huntington's disease can be developed using the platform 100. In this example, a brain metric can include a HTT gene (CAG trinucleotide repeat) mutation model using mutant iPSC-medium spiny neurons (MSNs) (e.g., GABAergic neurons).

Treatments for Lewy body dementia can be developed using the platform 100, such as with NVU 800. This disease includes dementia with Lewy bodies, and is the second most common dementia after AD. Brain metrics can include measurements of cortical neurons. The disease can be induced in the NVU 800 using A53T mutant alpha-synuclein.

Treatments for frontotemporal dementia (FTD) can be developed using the platform 100, such as with NVU 800. For example, iPSC-cortical neurons with any of the following genetic mutations can be tracked as brain metrics: TAR DNA-binding protein of about 43 kDa (TDP-43); progranulin (PGRN); and Charged Multivesicular Body Protein 2B (CHMP2B).

Treatments for amyotrophic lateral sclerosis (ALS) can be developed using the platform 100, such as with NVU 800. For example, iPSC-motor neurons with any of the following mutations can be used as brain metrics: superoxide dismutase (SOD1); TDP-43; and chromosome 9 open reading frame 72 (C9ord72).

Treatments for spinal muscular atrophy (SMA) can be developed using the platform 100, such as with NVU 800. For example, iPSC-motor neurons with the following mutations can be used as brain metrics: SM41; and ubiquitin-activating enzyme 1 (UBE1).

Figure 9:
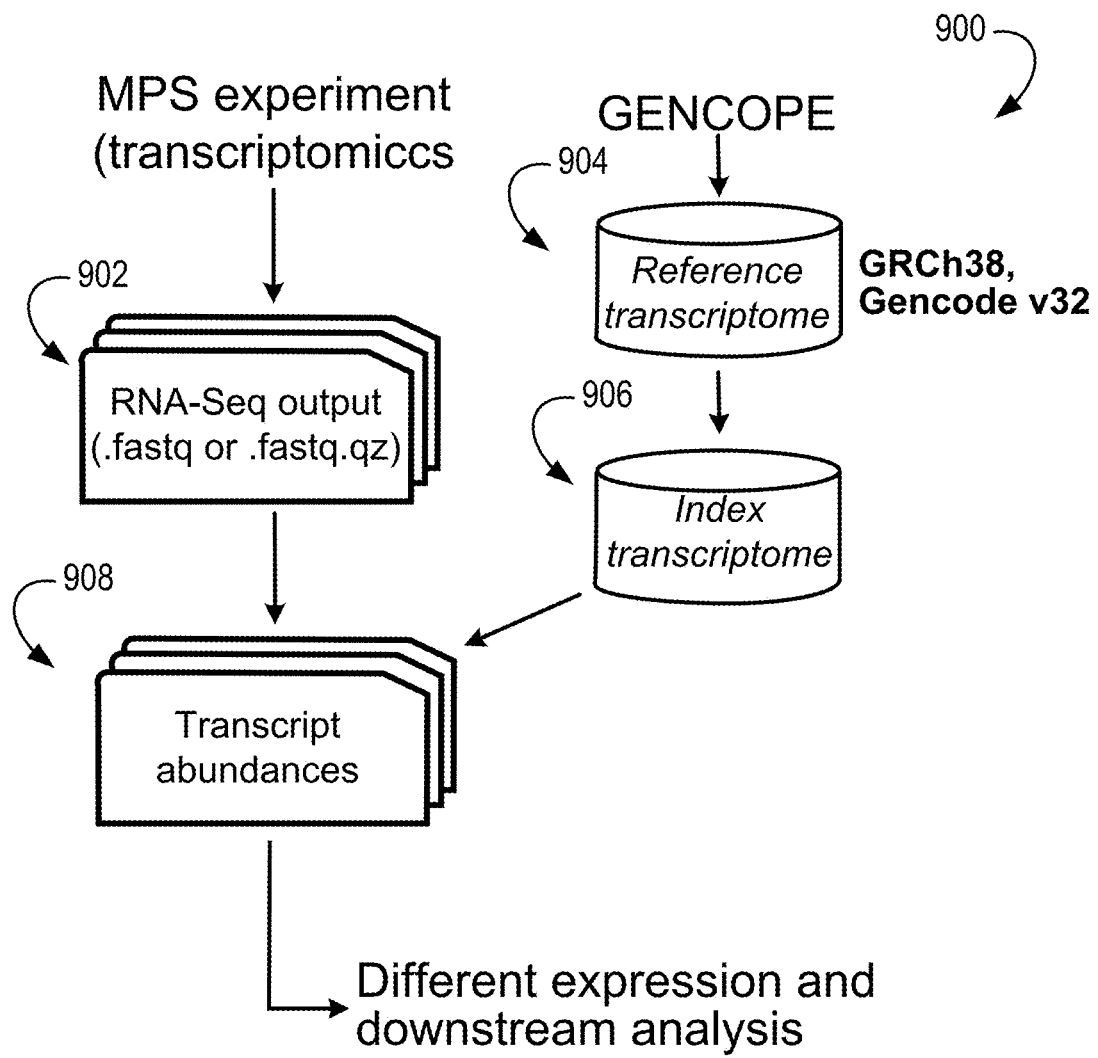
FIGS. 9-14 are flow diagrams illustrating example processes for analysis of MPS data for preclinical drug discovery system for developing treatments (e.g., drugs) for neurodegenerative diseases.

Turning to FIG. 9, a process 900 includes a process for MPS transcriptomics data generation and analysis. The process includes generating RNA-Seq data 902 (transcriptomics) for differential gene expression studies using MPS cultured tissue samples. The process 900 includes generating RNA-Seq data 902 for healthy and disease MPSs. The process 900 includes acquiring raw RNA-Seq files 902 (e.g., fastq or compressed fastq) from next generation sequencing (NGS). The process 900 includes importing a human reference transcriptome 904 (e.g., from Ensembl or Gencode) to map the sequencing data. In an example, a Gencode GRCh38 can be used as the reference transcriptome. The process 900 includes indexing 906 the reference transcriptome to prepare for transcript alignment and quantification. The process 900 includes implementing salmon pseudo-alignment and transcript quantification algorithm 908 to calculate transcript abundances. Summarize transcript abundances to gene level using the reference transcriptome. Generated gene counts for each sample can be normalized and differential expression analysis can be implemented using the DESeq2 method. Genes with log 2 fold-change threshold of 1 and adjusted p-value threshold of 0.05 are considered as differentially expressed genes (DEGs). DEGs between the healthy and disease phenotypes are used for downstream (functional) analysis using hypergeometric or Fischer's exact test (statistical models) to determine pathway enrichments associated with the disease. Pathway information can be imported from Gene Ontology (GO), KEGG, and Reactome annotations and biological pathway databases.

Figure 10:
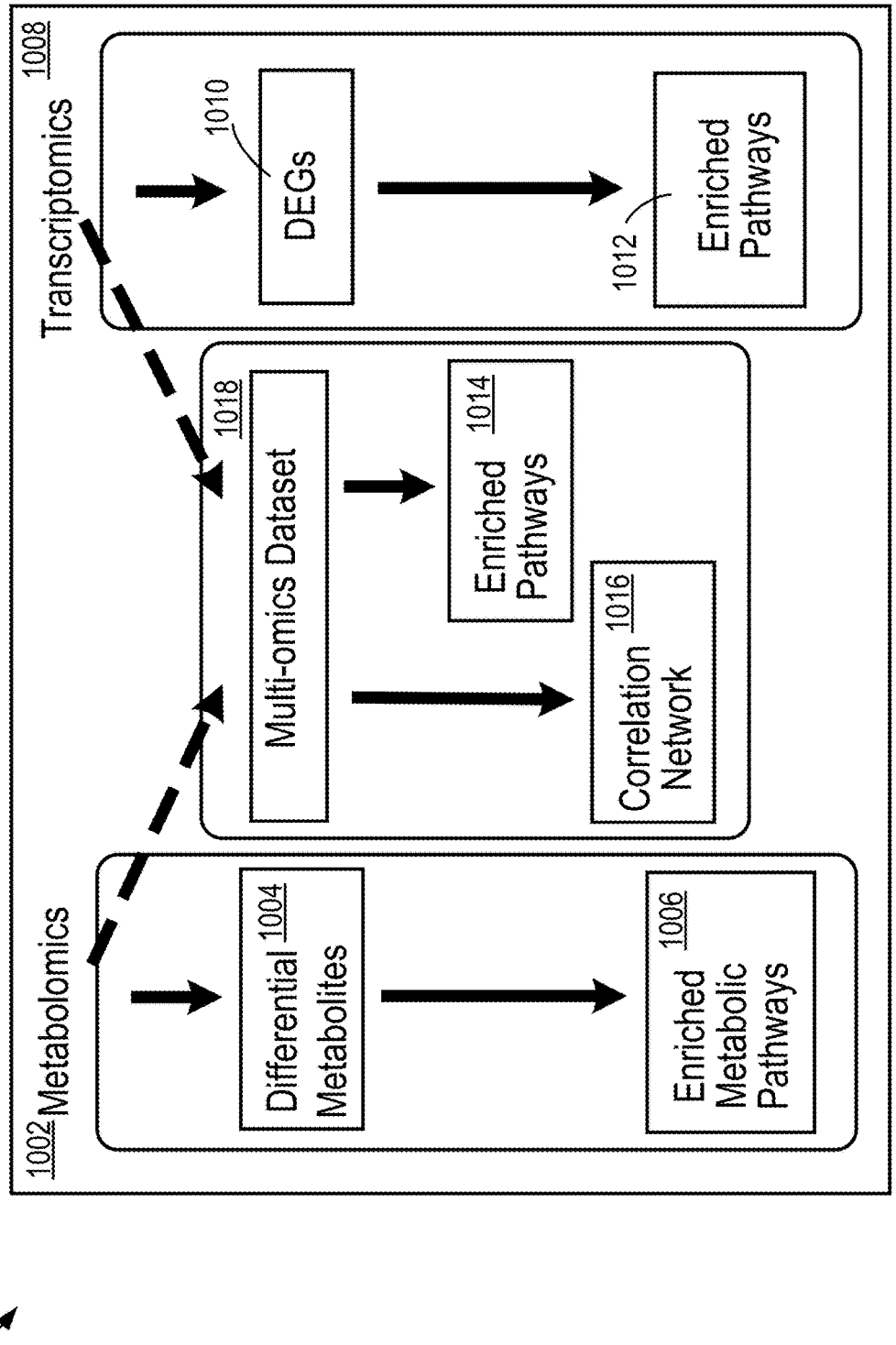

FIG. 10 shows an example of a process 1000 for MPS metabolomics & transcriptomics data analysis and integration. The process 1000 includes analysis of the transcriptomics data according to process 900 of FIG. 9. The process 1000 includes analyzing metabolomics data 1002 generated from the MPSs (healthy vs disease) to determine significant metabolite alterations. Metabolites with log 2 fold-change threshold of 1 and adjusted p-value threshold of 0.05 are considered as differential metabolites 1004 for the healthy and disease phenotypes. The process 1000 includes using the differential metabolite 1004 data to implement hypergeometric or Fischer's exact test (statistical models) to determine metabolic pathway enrichments 1006 associated with the disease (e.g., PD or other neurodegenerative disease). Pathway information can be imported from KEGG and Reactome biological pathway databases.

Generally, if there are at least two omics layers (such as metabolomics 1002 and transcriptomics 1008), datasets can be combined to generate multi-omics datasets. Multi-omics datasets 1018 can be analyzed using the hypergeometric or Fischer's exact test for pathway enrichment 1014 or using a pathway-free approach to build correlation networks 1016 for integrated omics analysis. Omics analysis results can be used both in Systems Biology and QSP workflows. The transcriptomics data 1008 can be used alone to generate DEGs 1010 and enriched pathways 1012.

Figure 11:
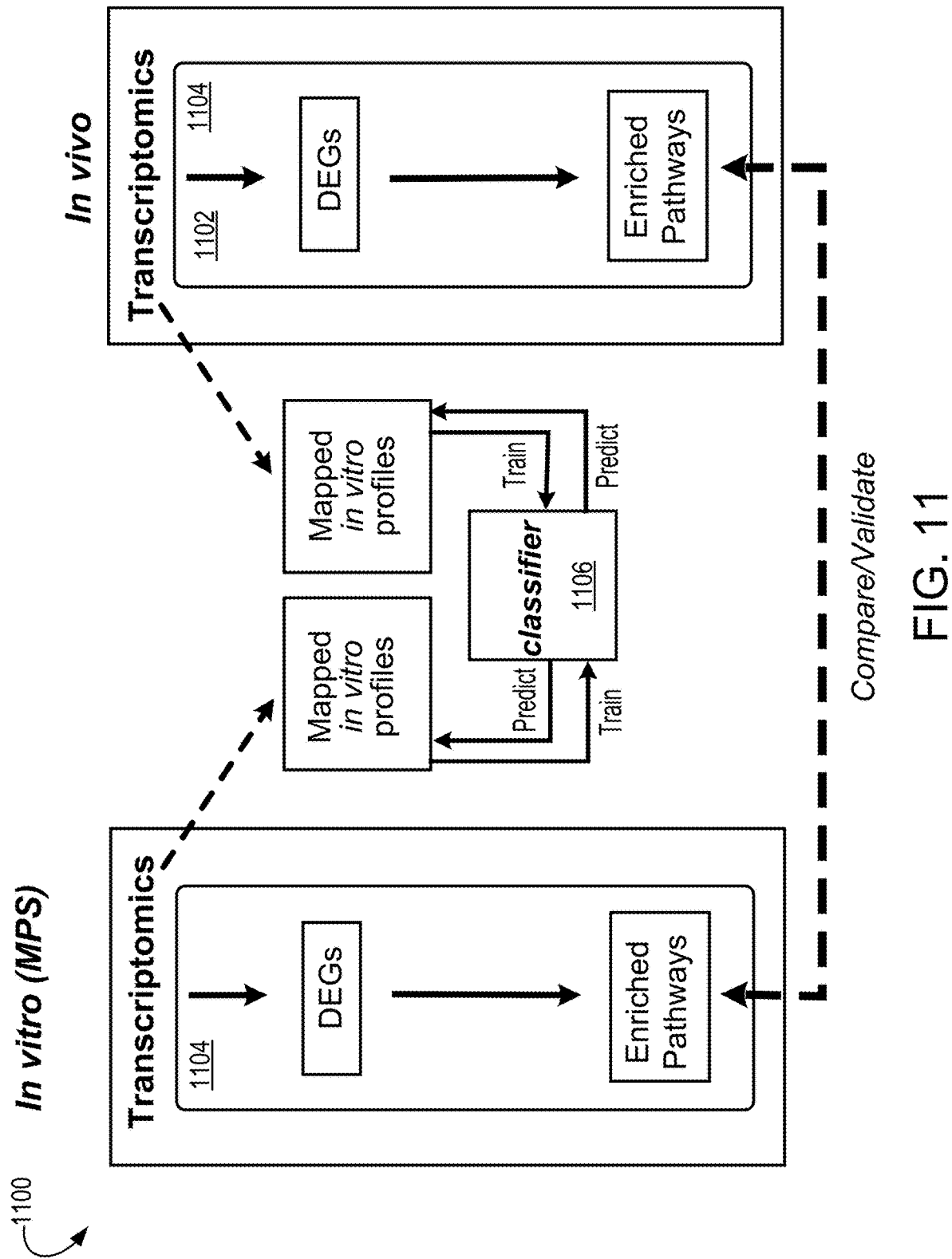

FIG. 11 shows an example process 1100 for NVU-to-human translation steps for in vitro disease model validation. Generally, a major consideration in developing a complex human in vitro model is conservation and regulation of gene expression as measured in human tissues. This is performed for studying human diseases and disorders and for the potential use of these complex in vitro models as target discovery platforms. To evaluate the similarity and relevance of the MPSs to human tissues, the system is configured to evaluate gene expression datasets of MPSs to clinical datasets. Public repositories, such as the National Center for Biotechnology Information (NCBI) Gene Expression Omnibus (GEO), can be used to extract human tissue datasets to develop MPS-to-human translation model, a framework of translational machine learning (ML) models. A similar approach can be taken for translation of animal model studies to human (clinical) findings. The MPS-to-human translational effort identifies MPS phenotypes for better translation to human disease stages and observations. Using this framework, potential human-disease genes are discoverable using MPS data.

Generally, for process 1100, the MPS transcriptomics data are analyzed as described in relation to FIGS. 9-10. In vivo transcriptomics datasets 1102 for healthy and disease conditions are gathered from databases, such as the National Center for Biotechnology Information (NCBI) Gene Expression Omnibus (GEO) public repository. In vitro (MPS) datasets 1104 and in vivo datasets are compared based on the pathway enrichments observed for healthy vs disease phenotypes. Pathway enrichment methods are described in relation to FIG. 10.

For MPS-to-human translation, to predict the in vivo gene expression from an in vitro (MPS) gene expression data using a regression model, at least one of the following algorithms can be used: lasso or elastic net regression, decision trees, and neural networks. ML algorithms are described in greater detail with respect to FIG. 15. The algorithm can translate disease modifications and target perturbations measured in the MPS to in vivo outcomes (effects). For example, the ML approach can be used to train and test a classifier 1106 based on at least one of the following algorithms: logistic regression, support vector machines, random forest, and neural networks. The classifier 1106 is trained using both datasets to classify healthy and disease phenotypes using transcriptomics data. Generally, the process 1100 includes evaluating and comparing performance of the models using the following metrics: area under receiver operating characteristic (ROC) curve (AUC) and root-mean-square-error (RMSE).

Figure 12:
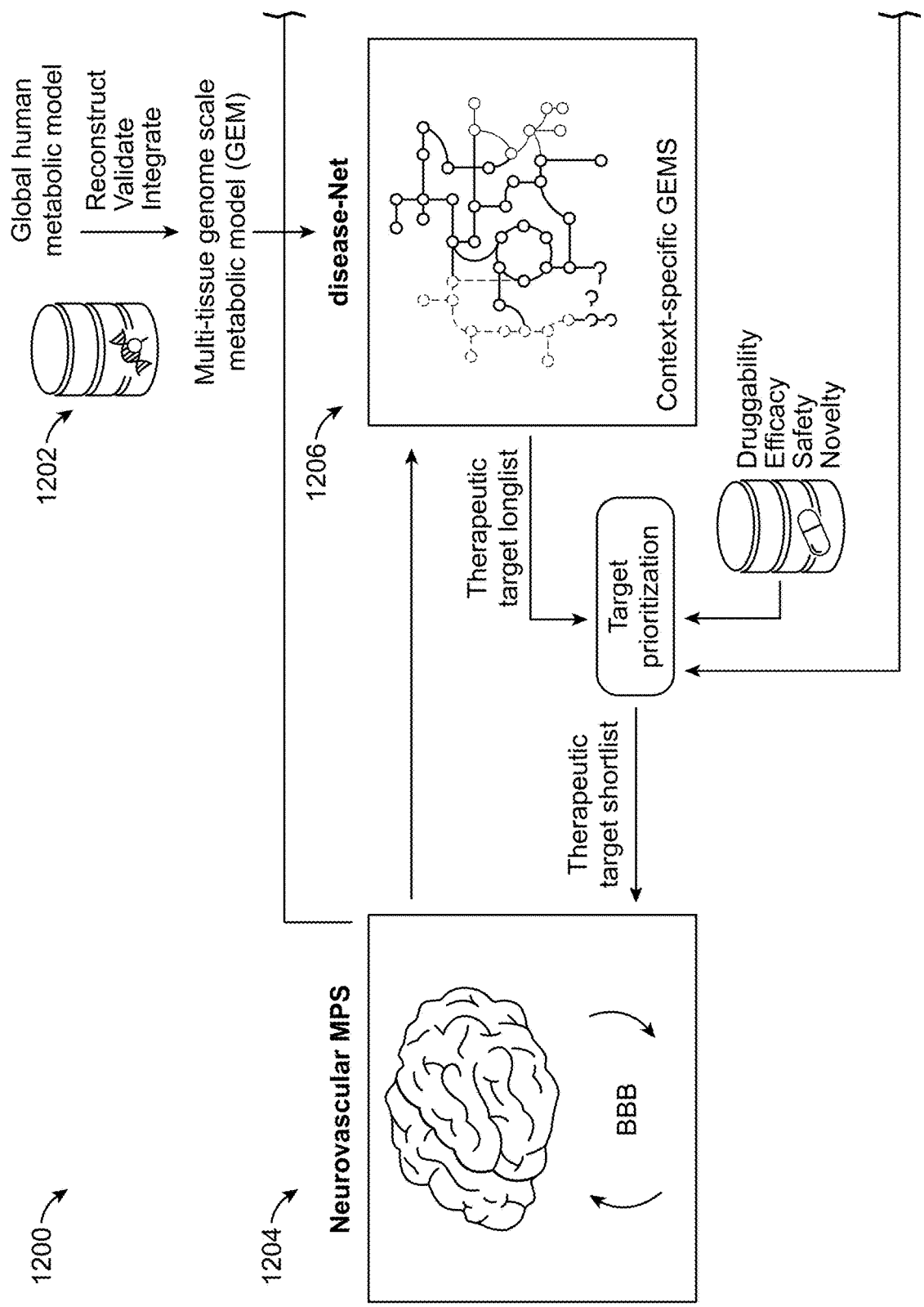
Figure 12:
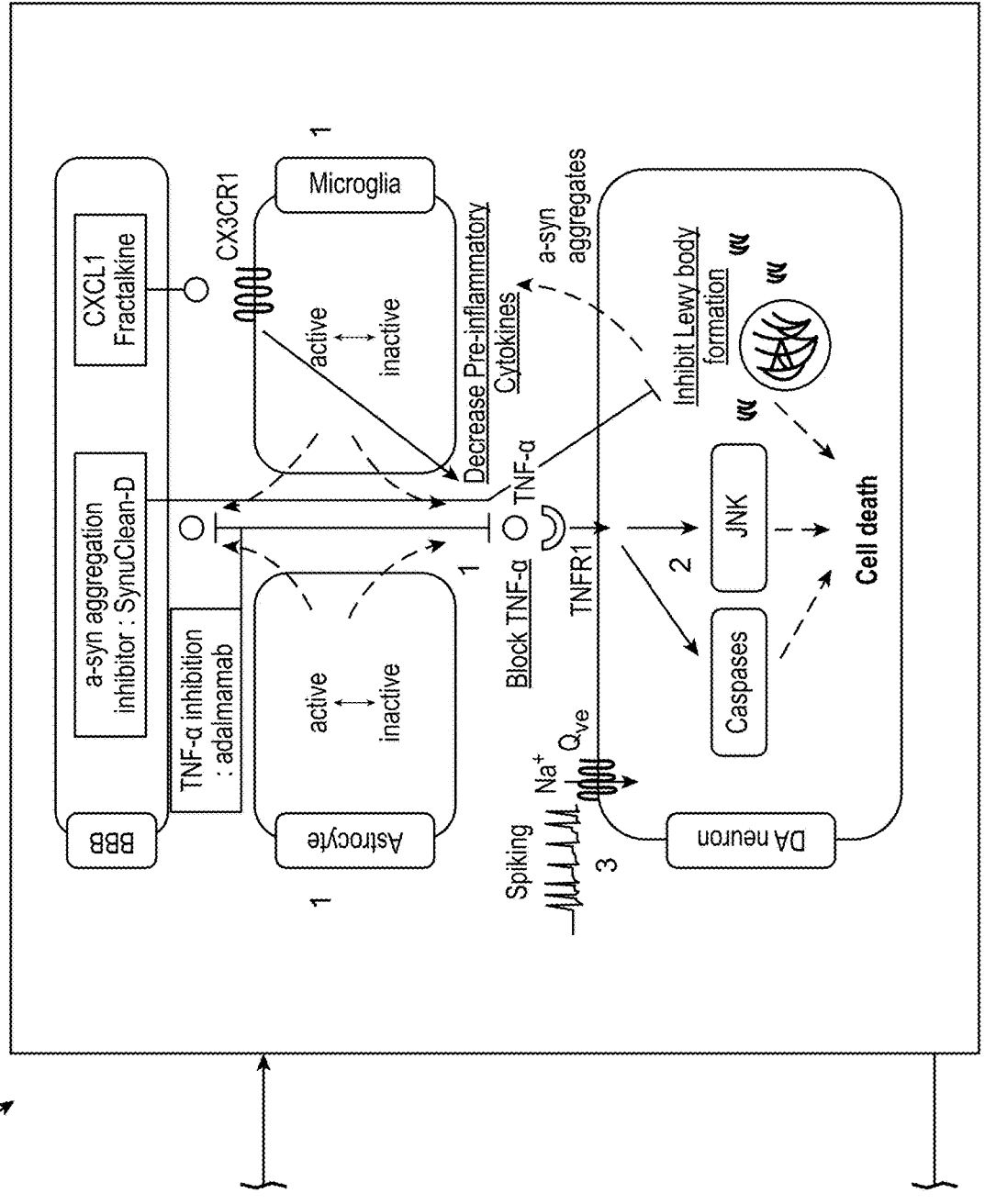

FIG. 12 shows an example process 1200 for target discovery computational workflows. In this example, SB, QSP, or both can be used. Computational algorithms enable the system to perform mapping of high-content (-omics data) and high-throughput data from NVUs (e.g., NVU 110 previously described) and characterization of molecular disease signatures. For target discovery efforts, a disease-Net computational framework is used. The computing system performs pathway-based integration of omics datasets with computational framework of genome-scale metabolic models (GEMs) to analyze disease pathophysiology.

Generally, GEMs stratify distinct biological profiles by linking genotypes to phenotypes through gene-protein-reaction associations. These GEMs for individual tissues or cell types are constructed from global human metabolic network models (e.g., Human Metabolic Reaction (MR 2.0) or Recon 3D, etc.). Tissue-specificity information from public databases (e.g., UniProt and Human Protein Atlas, etc.), and internal MPS gene expression data are used to construct the GEMs. For multiple-tissue GEMs, individual tissue models are mathematically connected through a common pool compartment that represent the media used in the MPS experiments. The network model forms a scaffold to map and analyze big data, to run simulations for different metabolic states of the tissues and to generate hypotheses on disease associated mechanisms for target discovery.

Application of this approach using the MPS platforms gives flexibility, relative to big data generated from human biopsy or tissue samples, on the type and amount of data that can be generated from individual tissues at any stage of the disease. Each phenotype (such as healthy or diseased) can include a different GEM construction, which is referred to as "context-specific GEMs". Using these GEMs, metabolic states for healthy and disease phenotypes can be compared to elucidate disease progression and differential reactions. Based on the differential signatures in phenotypes, candidate therapeutic target list is generated. These therapeutic targets may consist of mRNAs, proteins and metabolites, which are indirectly or directly associated with metabolic reactions, as well as metabolites (compounds) to be supplemented due to disease-related deficiency. The long lists of targets can then be rank-ordered to prioritize with respect to several criteria such as druggability, therapeutic evidence in clinical data, tissue specificity, safety/toxicity information, and novelty. We use efficacy, safety, and novelty information from public databases such as DrugBank, Therapeutic Target Database (TTD), Open Targets, and PHAROS for target prioritization. As a result of prioritization, therapeutic target shortlists are generated to be experimentally validated using the MPS.

The process 1200 includes constructing (1202) the GEMs. To do this, the computing system imports generic human metabolic network models from databases & public repositories (e.g., Human Metabolic Reaction, Recon 3D, etc.). The computing system refines and reconstructs the generic human metabolic network model for the cell/tissue types in the neurovascular MPS by preserving the gene-protein-reaction associations using tissue-specificity information from databases (e.g., Human Protein Atlas, UniProt, etc.). The computing system validates the tissue-specific genome scale metabolic models (GEMs) by confirming network connectivity and running metabolic simulations under steady-state conditions. If there are at least two tissue- or cell-type-specific GEMs, the computing system integrates the GEMs by modeling a common pool compartment for nutrient of small molecule exchange, which mimics the culture media in any given in vitro experiment. The resulting integrated GEM is a scaffold on which to map MPS data.

The process 1200 includes generating (1204) MPS data. The computing system is configured to cause generation of transcriptomics data for gene expression using the MPS for healthy and (at least one disease stage of) disease phenotypes. Additionally, the computing system is configured to cause generation of untargeted intracellular metabolomics data using tissue samples cultured in the MPS.

The process 1200 includes mapping (1206) MPS data on GEMs. Using the healthy transcriptomics data, the computing system validates the tissue-specific GEM by confirming network connectivity and running metabolic simulations under steady-state conditions. If (at least one stage of) disease is analyzed, the computing system maps the disease MPS data on the integrated GEM. The resulting validated integrated GEMs are referred to as a disease-Net framework. The computing system determines differential reactions in healthy and disease states, by comparing healthy and disease GEMs. The computing system determines the proteins (enzymes) that regulate these differential reactions and lists them as candidate therapeutic targets. If generated, the computing system integrates the MPS metabolomics data to validate the disease-Net framework by confirming that every experimentally measured metabolite is consumed and produced in the integrated GEMs. If generated, the computing system uses the MPS metabolomics data to validate the candidate therapeutic targets. The targets were determined based on transcriptomics data, and metabolomics facilitate confirmation as to whether an altered gene expression results in a perturbation in a reaction regulated by that gene's product (enzyme). The resulting list is called a "therapeutic target longlist".

Figure 13:
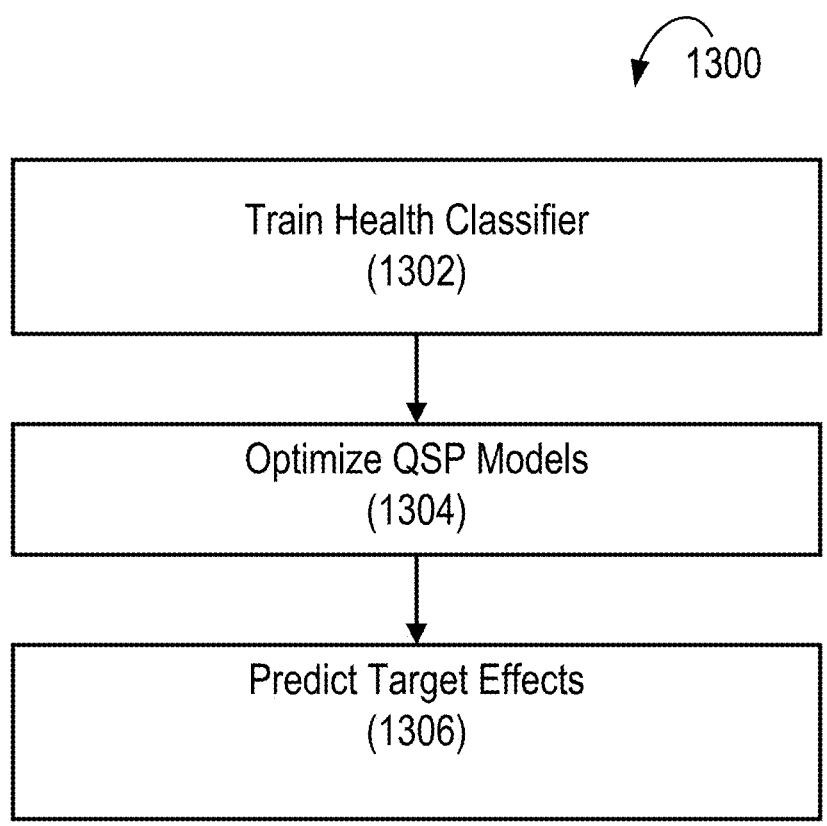

FIG. 13 shows an example process 1300 for QSP-based computational target discovery. The process 1300 includes training (1302) a health classifier. Training the classifier can include using both "healthy" and "disease" MPS data. Once trained, the classifier predicts whether a new set of phenotypic metrics were produced by a "healthy" or "disease" system. The process 1300 includes optimizing (1304) the QSP models. The QSP model includes mechanisms identified by omics analysis (e.g., healthy vs. disease MPS data from the NVUs previously described). The computing system optimizes parameters separately to fit phenotypic metrics from healthy MPS and the disease MPS. Once optimized, the QSP models produce the phenotypic metrics observed in the MPSs. The process 1300 includes predicting (1306) target effects. Each of the disease QSP model and the healthy QSP model are used to make predictions. The computing system is configured to simulate hypothetical target perturbations and identify those perturbations which transition a "disease" QSP model to a "healthy" class. The computing system proposes experiments to rescue healthy phenotypes for the "disease" MPS (e.g., an NVU previously described).

At least some phenotypic metrics, but in some implementations, all of the phenotypic metrics, from both healthy and disease MPSs, are used to train a classifier (e.g., support vector machine, linear discriminant analysis, neural networks, etc.). The trained classifier will predict whether a new set of metrics represents a healthy or disease phenotype. Phenotypic data (described before), such as multi-electrode neural activity (MEA), extracellular concentrations (cytokines, reactive oxygen species, cell death) are generated for healthy and disease MPSs.

The computing system constructs a mechanistic (ODE-based) QSP model to simulate experimental MPS data (phenotypic and -omics), as subsequently described in relation to FIG. 14. A single set of equations (i.e., differential, algebraic, logic, and statistical) for the QSP model represents a set of causal physiological processes that may differ between the healthy and disease MPSs. Generally, two sets of parameters are obtained for the QSP model equations to capture the differences in the putative disease processes between healthy and disease MPSs. First, the QSP model parameters are adjusted using parameter estimation algorithms (e.g., non-linear least squares, Bayesian inference, evolutionary algorithms, etc.) to make the simulated phenotypic metrics match the phenotypic metrics from the healthy MPS. Those parameters, along with the QSP equations, define the healthy QSP model. Independently, the QSP model parameters are adjusted to fit the phenotypic metrics from the disease MPS. Those parameters, along with the same equations, define the disease QSP model.

The computing system is configured to simulate computational target perturbations in the QSP model to evaluate targets that can improve the disease phenotype. The same perturbations are applied to the healthy and disease QSP models, and the phenotypic output is classified using the same classifier that is trained on the MPS data. The computing system identifies perturbations that transition the disease QSP model from disease to healthy class without transitioning the class of the healthy QSP model. Simulated perturbations may represent target manipulations directly, like chemical (e.g., receptor agonists, antagonists) or physical (electrical and optical) perturbations. Successful simulated perturbations directly predict target effects that can rescue the healthy phenotype in the disease MPS. Alternatively, simulated perturbations can represent more abstract phenomenological changes (e.g., changes to biophysical properties, like membrane capacitance). More detailed QSP models are constructed subsequently to simulate mechanistic target manipulations that cause the same effects identified using the more abstract phenomenological model. Experiments predicted by QSP simulation to improve phenotype in the disease MPS can be tested in the high-throughput workflow.

Figure 14:
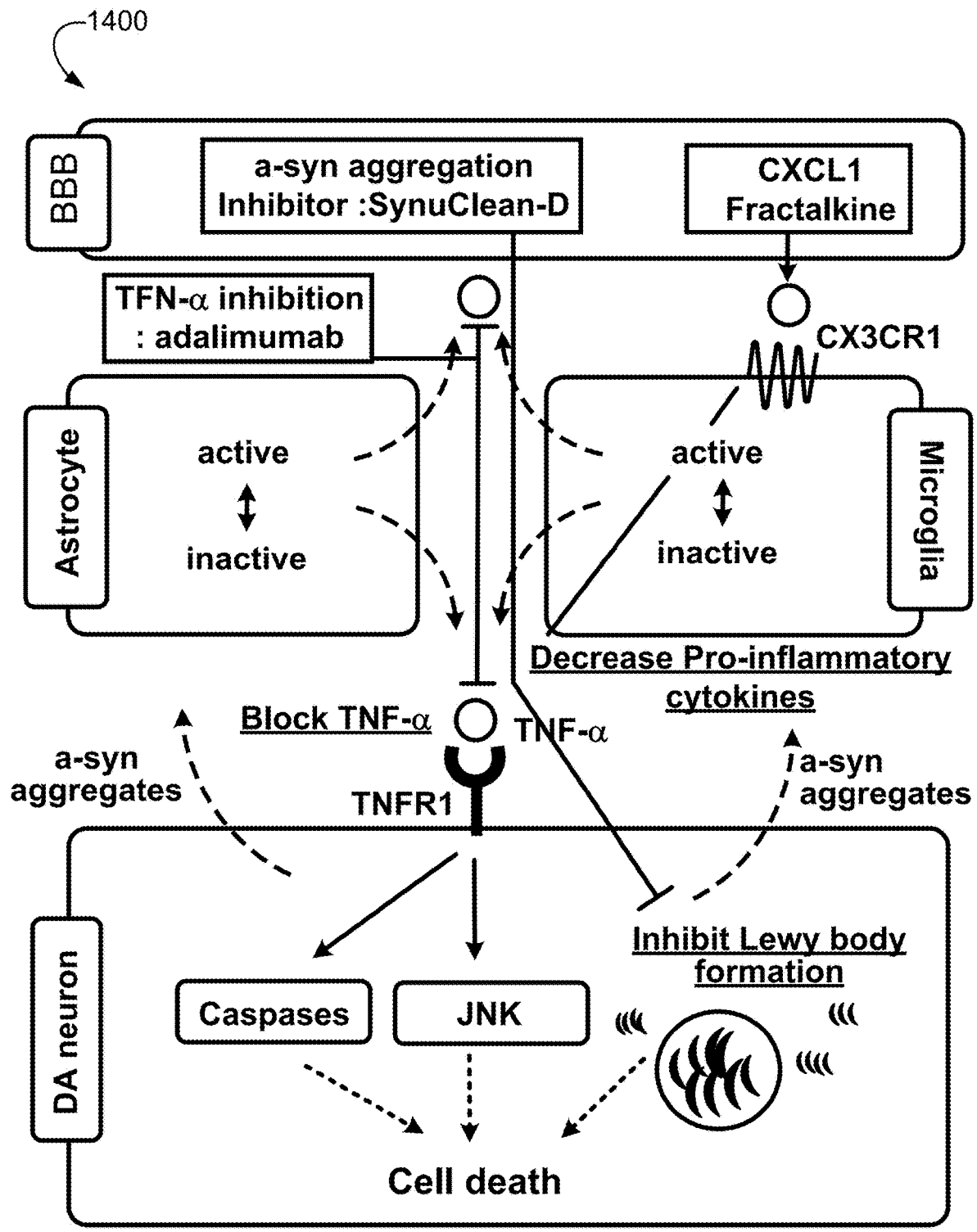

FIG. 14 shows a process for QSP model construction by the computing system. Generally, ODE-based QSP models combine diverse sources of information into a causal framework that can predict the effects of manipulating hypothetical targets. MPS manipulations are used by the computing system to identify tissue-scale components (e.g., cell types, extracellular processes, intercellular signaling pathways) that contribute to disease pathophysiology and are to be incorporated in the QSP model. For example, cell types and inter-cellular signaling pathways are generally informed by phenotypic regression analysis from the leave-one-(cell-type)-out experiments and experiments with receptor agonists and antagonists.

Systems biology methods are used by the computing system to identify intracellular mechanisms (such as signal transduction pathways, biophysical processes) that contribute to disease pathophysiology and need to be incorporated in the QSP model. For example, the multi-omics data set analysis may reveal enriched pathways that are differentially modulated in disease. Those insights can be combined with prior knowledge on canonical pathways to construct a set of mechanistic equations that capture the physiological processes implicated in disease. When multiple disease MPSs are present, the QSP model may be further constrained to include only the pathways that are modulated in all disease MPSs.

Neuronal biophysical models may be informed by differential expression of transmembrane proteins (ion channels, pumps, receptors), identified by transcriptomics, or by changes in ATP-dependent processes, suggested by differences in metabolic networks derived from healthy and disease MPSs. Differences in electrophysiology (e.g., firing rate, interburst interval, network synchrony) between healthy and disease MPS will be characterized. Observed differences may be combined with prior knowledge on cell-type specific biophysics (e.g., kinetics of potassium and sodium channels, membrane capacitance) to further constrain biophysical details (e.g., ion channel conductance, time constants) of the QSP model.

Returning to FIG. 12, the computing system applies (1208) the QSP models for target prioritization. For example, if the "therapeutic target longlist" is too long or not ordered, targets can be rank-ordered based on several criteria, such as tissue-specificity, druggability, efficacy/safety, novelty, etc. A scoring system uses the abovementioned criteria to rank-order the therapeutic targets to be tested experimentally. Databases (e.g., DrugBank, Therapeutic Target Database (TTD), Open Targets, PHAROS, etc.) are referenced to extract druggability, and efficacy/safety information for each target. Based on the information from the databases and the target effects predicted by QSP simulation (e.g., health class transitions), the computing system assigns to undruggable and toxicity-inducing targets negative scores (e.g., lower scores) for these criteria, while druggable, safe and disease modifying targets are assigned positive scores (e.g., higher scores). If information is missing for a criterion, no score is assigned. The therapeutic target longlist can be rank-ordered based on the scores and target validation experiments will be proposed based on this prioritized target list (target shortlist).

For experimental target validation, shortlisted therapeutic targets (either mono or combo targets) are perturbed in healthy and disease MPS to validate (evaluate) their disease modifying potential. The target perturbations may include xenobiotics, biologics, RNAi, CRISPR sgRNA addition to healthy or disease NVU MPS. Generally, phenotypic metrics are quantified to assess disease modification. In some instances, multi-omics datasets can be generated and quantified to assess or confirm disease modification.

The processes 900, 1000, 1100, and 1200 can be used for treating PD, using the NVU MPSs previously described. To validate the NVUs ability to identify therapeutic mechanisms of action (MoA), evaluation of well-characterized drugs is performed for their phenotypic and transcriptomic effects. Pathophysiology often depends on cell-cell interactions and the cellular microenvironment. Phenotypic and transcriptomic data generated with the NVU PD MPSs provides cell-specific, mechanistic insights into the complex, multi-cellular interactions that underlie PD progression by integrating the NVU PD MPS data with other sources of mechanistic information (e.g., target characteristics and drug properties). A PD-specific MIDD framework uses the systems biology (SB) and QSP models. The models identify the right pathway, right target, right molecule, right dose, and right patients using multi-donor, multi-scale MPS data, as previously described.

In an aspect, the NVU PD MPSs previously described are acutely treated with drugs to determine their phenotypic (electrical, cytokine, apparent permeability, etc.) and transcriptomic effects. The drugs are tested at five concentrations spanning a nanomolar to millimolar range to develop a dose-response relationship. Where applicable, the drugs are dosed on the blood-side of the BBB to determine the pharmacokinetic and biodistribution profiles in healthy and diseased conditions. Drug concentrations in the systems are maintained during the duration of the experiment by adding drug during media changes. The drugs evaluated are selected based on their clinical significance for treating Parkinson's disease and for their established MoA (e.g., neuromodulatory, oxidative stress, cytokine production, etc.). Specifically, DA receptor activation is targeted using DAR agonists like bromocriptine, rotigotine, etc. in the striatal NVU MPS. Additionally, in the SNpc NVU MPS, α-synuclein aggregate formation is targeted using SynuClean-D, neuroinflammation and apoptosis using the Cx3CR1 ligand CX3CL1 (fractalkine), and the TNF-α inhibitor adalimumab (Humira). The transcriptomic data will be evaluated using our existing SB models.

First, the computing system determine mechanisms relevant to Parkinson's disease and integrates them in a computational model. The structure of the mechanistic QSP model is informed by prior clinical knowledge and the NVU MPS data analysis. Mechanisms previously identified and phenotypic markers modulated by disease are included in the model. Additional known pathways are incorporated as needed to model the data.

Second, the NVU MPS is perturbed experimentally using drugs with known mechanisms of action. Phenotypic metrics are used to optimize and qualify the QSP model. Kinetic parameters will be fit based on changes in the functional readouts. For instance, a drug acting causally on mechanism X to influence functional readout Y will be used to optimize kinetic parameters that couple the effects of X to Y. Multiple parameters can be optimized simultaneously by fitting the model using all of the functional readouts. Parameters for specific intercellular crosstalk mechanisms can be quantified by preparing NVU MPSs with fewer cell types (leave-one-out approach). Once qualified by experimental MPS data, the QSP model can be used to predict the system-wide result of complex interactions driven by novel perturbations. The qualified model is called the PD-Sim module.

Third, the perturbations are parameterized and discovery re-casted as a model-based optimization problem. The PD-Sim module will be initialized in the disease state based on the observed PD phenotype. The desired state is defined by the phenotype observed in the healthy NVU MPS. The benefit of simulated perturbations targeting disease pathways is assessed by comparing the resulting model phenotype to the desired phenotype. Using this approach, novel targets and beneficial molecular properties are identified based on molecular perturbations that minimize the difference between healthy and perturbed phenotypes in PD-Sim.

For quantifying the PD phenotype, the mechanistic, cell-specific contributions to complex pathophysiology are characterized by the computing system using transcriptomic profiling. Changes in NVU transcriptome are measured using Illumina™ NGS technology. Human RNA-Seq assay analyzing the coding RNAs (mRNAs) is used to investigate gene expression in PD phenotypes in comparison with healthy NVU phenotypes, as previously described. The transcriptomic data sets generated from the PD NVU MPSs are analyzed using our transcriptomics data analysis workflow, as previously described. Exploratory analyses are performed using unsupervised approaches such as dimensionality reduction (e.g., PCA and MDS) and agglomerative hierarchical clustering to review phenotype-specific expression signatures, and for QC of batch-to-batch and sample-to-sample variance. Differential expression analysis is performed for further analysis of gene ontology (GO) and pathway enrichment to obtain semi-mechanistic insights on disease induction and progression at the transcription level.

The PD phenotype is rescued by integrating, by the computing system, the mechanistic data using the QSP framework to predict therapeutic molecular perturbations. The causal nature of the biological processes implicated in PD are assessed using QSP methods previously described. QSP provides a mechanistic framework for exploring the dynamic interactions between biological processes in silico.

First, intracellular and cell-cell interaction mechanisms by SB methods are integrated in QSP models. The dynamic interaction between cellular mechanisms are modeled using mass action and biophysical modeling. Receptor competition models are used to incorporate effects of drugs on disease-related physiology. Then, simulation studies are performed to obtain deeper insight into the role of incorporated mechanisms in etiology, modification, and prevention of PD. Further simulations can be performed to identify molecular properties and treatment regimens that will improve cellular phenotype.

The effects of standard of care therapeutics are evaluated on the phenotypic and transcriptomic profile of the striatal NVU PD MPS. DA agonists like bromocriptine are prescribed to compensate for the loss of DA neurons in the SNpc. Their action on DA receptors (DARs) in the striatum can restore healthy neurophysiology and alleviate symptoms. However, chronic administration can sensitize DARs in striatal MSNs and produce side effects like L-dopa-induced dyskinesia (LID). The response of striatal PD model to DA agonists can be analyzed. The striatal (MSN) NVU PD MPS are established. Following the system maturation period (~14 days), baseline neuronal electrical activity (MEA device) is recorded, and media reserved to determine oxidative stress and cytokine and ROS production. Next, the systems are treated with DAR agonists (blood-side of the BBB) using a dose-response strategy and evaluated for effects on neuron physiology for up to 14 days. Once the period of maximal neuronal recovery is determined, the cells from the drug-treated and control systems are harvested for transcriptomics analysis. Also, the permeability test is conducted by introducing the fluorescent dextran in the system to characterize the pathological BBB phenotype in this model. Finally, spent culture media are reserved from disease and healthy control MPSs to determine cytokine and ROS production. After all measurements are completed, endpoint assays are conducted. Phenotypic changes to the BBB are conducted 2. All data collected from these experiments are used to build and qualify the "Striatal PD-Sim" module. MIDD with Striatal PD-Sim is used to identify mechanisms that can manage symptoms and side effects.

The effects of disease phenotype-modifying therapeutics on the phenotypic and transcriptomic profile of the SNpc NVU PD MPSs are evaluated. PD progression involves proinflammatory glia-neuron crosstalk that increases DA cell death in SNpc. Therapeutic drugs with known mechanisms of action are used to alter the cell-cell interactions in a systematic way. These experiments validate the response of NVU PD MPSs to disease modifying drugs and to generate data for building and qualifying the "SNpc PD-Sim" module. The SNpc NVU PD MPSs are established. Following the system maturation period (~14 days), baseline neuronal electrical activity is recorded (e.g., by the MEA device), and media is reserved to determine oxidative stress and cytokine and ROS production. Next, the MPSs are treated with compounds (e.g., SynuClean-D, fractalkine (blood-side of the BBB), or adalimumab (Humira) (brain compartment)) using a dose-response strategy and evaluated for effects on neuron physiology for up to 14 days. Once the period of maximal neuronal recovery is determined (based on comparison to isogenic control systems), the cells from the NVU MPS drug-treated and control systems are harvested for transcriptomics analysis. The spent culture media are reserved from the drug-treated and control systems to determine cytokine and ROS production. Also, the permeability test is conducted by introducing the fluorescent dextran in the system to characterize the pathological BBB phenotype in this model. After all measurements are completed, endpoint assays are conducted. Phenotypic changes to the BBB are conducted. The mechanisms implicated by transcriptomics and functional readouts from all SNpc NVU MPS experiments contribute to the development of the SNpc PD-Sim module. Qualified SNpc PD-Sim is then used to predict novel perturbations that restore the healthy phenotype (e.g., decrease the activation of neuron death-promoting processes). Validation of disease modifying potential of the targets identified with SNpc PD-Sim can then be performed.

Figure 15:
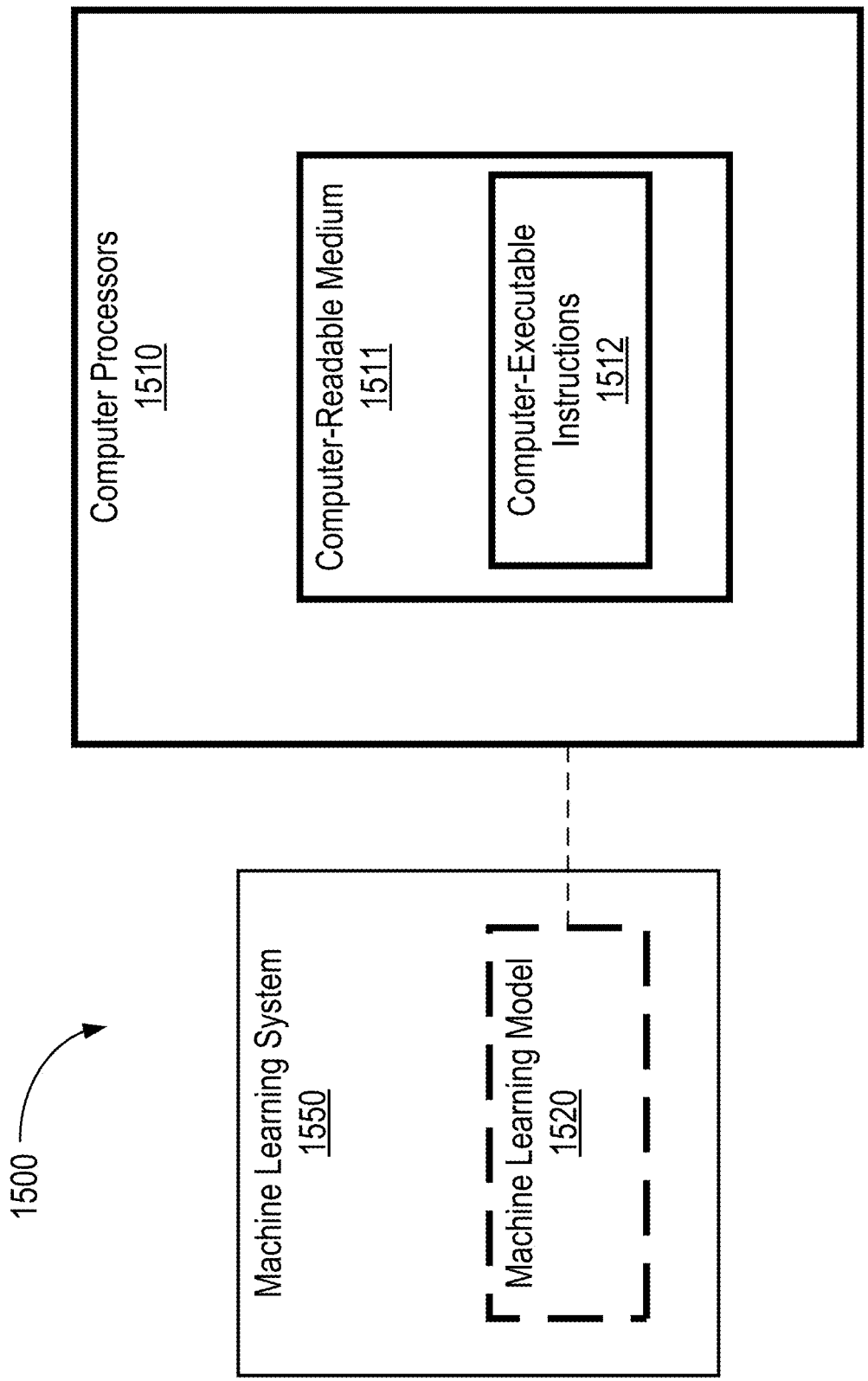
FIG. 15 is a diagram illustrating an example computer system configured to execute a machine learning model.

FIG. 15 is a diagram illustrating an example computer system 1500 configured to execute a machine learning model. Generally, the computer system 1500 is configured to process data indicating a phenotype and determine a class label ("healthy" or "disease") to predict the effect of a target on the state of the MPS. The system 1500 includes computer processors 1510. The computer processors 1510 include computer-readable memory 1511 and computer readable instructions 1512. The system 1500 also includes a machine learning system 1550. The machine learning system 1550 includes a machine learning model 1520. The machine learning model 1520 can be separate from or integrated with the computer processors 1510.

The computer-readable medium 1511 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an embodiment, the computer-readable medium 1511 includes code-segment having executable instructions.

In some implementations, the computer processors 1510 include a general purpose processor. In some implementations, the computer processors 1510 include a central processing unit (CPU). In some implementations, the computer processors 1510 include at least one application specific integrated circuit (ASIC). The computer processors 1510 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, etc., or a combination thereof. The computer processors 1510 are configured to execute program code means such as the computer-executable instructions 1512 and configured to execute executable logic that includes the machine learning model 1520.

The computer processors 1510 are configured to receive data indicating a molecular structure of, for example, a drug. The data can be obtained through one or more means, such as wireless communications with databases, optical fiber communications, USB, CD-ROM, and so forth.

The machine learning model 1520 is capable of processing the data to determine the class of phenotype ("healthy or disease"). In some implementations, the machine learning model 1520 is trained to determine class using a data set that includes MPS data (e.g., phenotypic, transcriptomic, etc.) and MPS labels. The machine learning model 1520 can classify the phenotype predicted by in vitro or in silico target perturbations. Accordingly, when a data set (in vitro or in silico) is introduced to the machine learning model 1520, it can predict whether an MPS platform exhibits a healthy or disease phenotype.

The machine learning system 1550 is capable of applying machine learning techniques to train the machine learning model 1520. As part of the training of the machine learning model 1520, the machine learning system 1550 forms a training set of input data by identifying a positive training set of input data items that have been determined to have the property in question, and, in some embodiments, forms a negative training set of input data items that lack the property in question.

The machine learning system 1550 extracts feature values from the input data of the training set, the features being variables deemed potentially relevant to whether or not the input data items have the associated property or properties. An ordered list of the features for the input data is herein referred to as the feature vector for the input data. In one embodiment, the machine learning system 1550 applies dimensionality reduction (e.g., via linear discriminant analysis (LDA), principle component analysis (PCA), or the like) to reduce the amount of data in the feature vectors for the input data to a smaller, more representative set of data.

In some implementations, the machine learning system 1550 uses supervised machine learning to train the machine learning models 1520 with the feature vectors of the positive training set and the negative training set serving as the inputs. Different machine learning techniques-such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments. The machine learning model 1520, when applied to the feature vector extracted from the input data item, outputs an indication of whether the input data item has the property in question, such as a Boolean yes/no estimate, or a scalar value representing a probability.

In some embodiments, a validation set is formed of additional input data, other than those in the training sets, which have already been determined to have or to lack the property in question. The machine learning system 1550 applies the trained machine learning model 1520 to the data of the validation set to quantify the accuracy of the machine learning model 1520. Common metrics applied in accuracy measurement include: Precision=TP/(TP+FP) and Recall=TP/(TP+FN), where precision is how many the machine learning model correctly predicted (TP or true positives) out of the total it predicted (TP+FP or false positives), and recall is how many the machine learning model correctly predicted (TP) out of the total number of input data items that did have the property in question (TP+FN or false negatives). The F score (F-score=2*PR/(P+R)) unifies precision and recall into a single measure. In one embodiment, the machine learning module iteratively re-trains the machine learning model until the occurrence of a stopping condition, such as the accuracy measurement indication that the model is sufficiently accurate, or a number of training rounds having taken place.

In some implementations, the machine learning model 1520 is a convolutional neural network (CNN). A CNN can be configured based on a presumption that inputs to the CNN correspond to image pixel data for an image or other data that includes features at multiple spatial locations. For example, sets of inputs can form a multi-dimensional data structure, such as a tensor, that represent color features of an example digital image (e.g., a biological image of biological tissue). In some implementations, inputs to the CNN correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the CNN can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which CNN performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R,G,B. A convolutional layer of a CNN of the machine learning model 1520 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the machine learning model 1520 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The machine learning model 1520 can then compute a dot product from the overlapped elements. For example, the machine learning model 1520 can convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The machine learning model 1520 can convolve each kernel over each input of an input volume. The machine learning model 1520 can perform this convolution operation by, for example, moving (or sliding) each kernel over each input in the region.

The machine learning model 1520 can move each kernel over inputs of the region based on a stride value for a given convolutional layer. For example, when the stride is set to 1, then the machine learning model 1520 can move the kernels over the region one pixel (or input) at a time. Likewise, when the stride is 2, then the machine learning model 1520 can move the kernels over the region two pixels at a time. Thus, kernels may be shifted based on a stride value for a layer and the machine learning model 1520 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the machine learning model 1520 can produce a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the CNN.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In some implementations, the spatial size of the output volume is computed as a function of the input volume size, W, using the formula (W−F+2P)/S+1. For example, an input tensor can represent a pixel input volume of size [227×227×3]. A convolutional layer of a CNN can have a spatial extent value of F=11, a stride value of S=4, and no zero-padding (P=0). Using the above formula and a layer kernel quantity of K=156, the machine learning model 1520 performs computations for the layer that results in a convolutional layer output volume of size [55×55×156], where 55 is obtained from [(227−11+0)/4+1=55].

The computations (e.g., dot product computations) for a convolutional layer, or other layers, of a CNN involve performing mathematical operations, e.g., multiplication and addition, using a computation unit of a hardware circuit of the machine learning model 1520. The design of a hardware circuit can cause a system to be limited in its ability to fully utilize computing cells of the circuit when performing computations for layers of a neural network.

Figure 16:
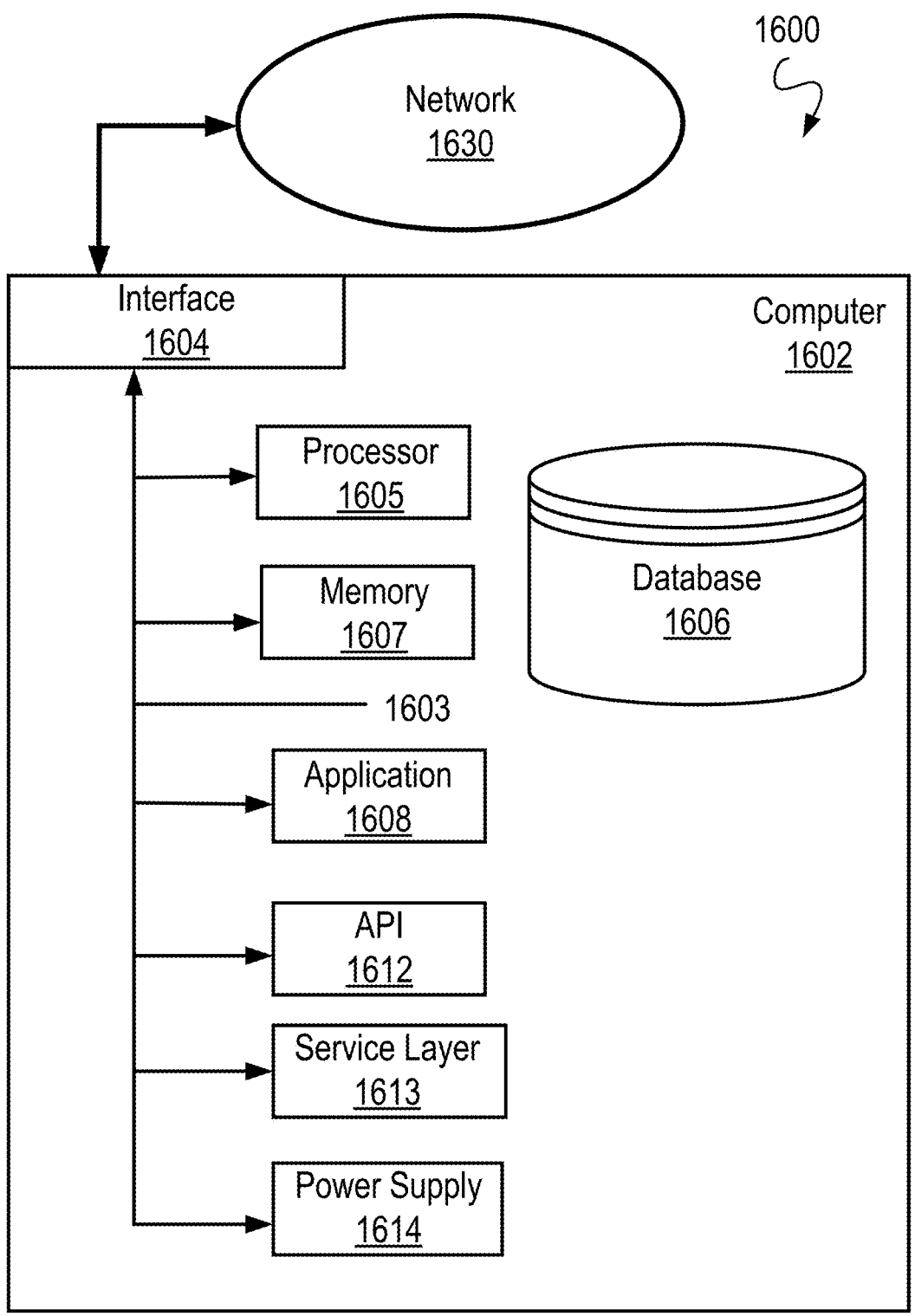
FIG. 16 is a block diagram of an example computer system used to provide computational functionalities associated with described algorithms, methods, functions, processes, flows, and procedures described in the present disclosure.

FIG. 16 is a block diagram of an example computer system 1600 used to provide computational functionalities associated with described algorithms, methods, functions, processes, flows, and procedures described in the present disclosure (such as the method 1300 described previously with reference to FIG. 13), according to some implementations of the present disclosure. The illustrated computer 1602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1602 can include input devices such as keypads, keyboards, and touch screens that can accept user information. Also, the computer 1602 can include output devices that can convey information associated with the operation of the computer 1602. The information can include digital data, visual data, audio information, or a combination of information. The information can be presented in a graphical user interface (UI or GUI).

The computer 1602 can serve in a role as a client, a network component, a server, a database, a persistency, or components of a computer system for performing the subject matter described in the present disclosure. The illustrated computer 1602 is communicably coupled with a network 1630. In some implementations, one or more components of the computer 1602 can be configured to operate within different environments, including cloud-computing-based environments, local environments, global environments, and combinations of environments.

At a high level, the computer 1602 is an electronic computing device operable to receive, transmit, process, store, and manage data and information associated with the described subject matter. According to some implementations, the computer 1602 can also include, or be communicably coupled with, an application server, an email server, a web server, a caching server, a streaming data server, or a combination of servers.

The computer 1602 can receive requests over network 1630 from a client application (for example, executing on another computer 1602). The computer 1602 can respond to the received requests by processing the received requests using software applications. Requests can also be sent to the computer 1602 from internal users (for example, from a command console), external (or third) parties, automated applications, entities, individuals, systems, and computers.

Each of the components of the computer 1602 can communicate using a system bus 1603. In some implementations, any or all of the components of the computer 1602, including hardware or software components, can interface with each other or the interface 1604 (or a combination of both), over the system bus 1603. Interfaces can use an application programming interface (API) 1612, a service layer 1613, or a combination of the API 1612 and service layer 1613. The API 1612 can include specifications for routines, data structures, and object classes. The API 1612 can be either computer-language independent or dependent. The API 1612 can refer to a complete interface, a single function, or a set of APIs.

The service layer 1613 can provide software services to the computer 1602 and other components (whether illustrated or not) that are communicably coupled to the computer 1602. The functionality of the computer 1602 can be accessible for all service consumers using this service layer. Software services, such as those provided by the service layer 1613, can provide reusable, defined functionalities through a defined interface. For example, the interface can be software written in JAVA, C++, or a language providing data in extensible markup language (XML) format. While illustrated as an integrated component of the computer 1602, in alternative implementations, the API 1612 or the service layer 1613 can be stand-alone components in relation to other components of the computer 1602 and other components communicably coupled to the computer 1602. Moreover, any or all parts of the API 1612 or the service layer 1613 can be implemented as child or sub-modules of another software module, enterprise application, or hardware module without departing from the scope of the present disclosure.

The computer 1602 includes an interface 1604. Although illustrated as a single interface 1604 in FIG. 16, two or more interfaces 1604 can be used according to particular needs, desires, or particular implementations of the computer 1602 and the described functionality. The interface 1604 can be used by the computer 1602 for communicating with other systems that are connected to the network 1630 (whether illustrated or not) in a distributed environment. Generally, the interface 1604 can include, or be implemented using, logic encoded in software or hardware (or a combination of software and hardware) operable to communicate with the network 1630. More specifically, the interface 1604 can include software supporting one or more communication protocols associated with communications. As such, the network 1630 or the interface's hardware can be operable to communicate physical signals within and outside of the illustrated computer 1602.

The computer 1602 includes a processor 1605. Although illustrated as a single processor 1605 in FIG. 16, two or more processors 1605 can be used according to particular needs, desires, or particular implementations of the computer 1602 and the described functionality. Generally, the processor 1605 can execute instructions and can manipulate data to perform the operations of the computer 1602, including operations using algorithms, methods, functions, processes, flows, and procedures as described in the present disclosure.

The computer 1602 also includes a database 1606 that can hold data for the computer 1602 and other components connected to the network 1630 (whether illustrated or not). For example, database 1606 can be an in-memory, conventional, or a database storing data consistent with the present disclosure. In some implementations, database 1606 can be a combination of two or more different database types (for example, hybrid in-memory and conventional databases) according to particular needs, desires, or particular implementations of the computer 1602 and the described functionality. Although illustrated as a single database 1606 in FIG. 16, two or more databases (of the same, different, or combination of types) can be used according to particular needs, desires, or particular implementations of the computer 1602 and the described functionality. While database 1606 is illustrated as an internal component of the computer 1602, in alternative implementations, database 1606 can be external to the computer 1602.

The computer 1602 also includes a memory 1607 that can hold data for the computer 1602 or a combination of components connected to the network 1630 (whether illustrated or not). Memory 1607 can store any data consistent with the present disclosure. In some implementations, memory 1607 can be a combination of two or more different types of memory (for example, a combination of semiconductor and magnetic storage) according to particular needs, desires, or particular implementations of the computer 1602 and the described functionality. Although illustrated as a single memory 1607 in FIG. 16, two or more memories 1607 (of the same, different, or combination of types) can be used according to particular needs, desires, or particular implementations of the computer 1602 and the described functionality. While memory 1607 is illustrated as an internal component of the computer 1602, in alternative implementations, memory 1607 can be external to the computer 1602.

The application 1608 can be an algorithmic software engine providing functionality according to particular needs, desires, or particular implementations of the computer 1602 and the described functionality. For example, application 1608 can serve as one or more components, modules, or applications. Further, although illustrated as a single application 1608, the application 1608 can be implemented as multiple applications 1608 on the computer 1602. In addition, although illustrated as internal to the computer 1602, in alternative implementations, the application 1608 can be external to the computer 1602.

The computer 1602 can also include a power supply 1614. The power supply 1614 can include a rechargeable or non-rechargeable battery that can be configured to be either user- or non-user-replaceable. In some implementations, the power supply 1614 can include power-conversion and management circuits, including recharging, standby, and power management functionalities. In some implementations, the power-supply 1614 can include a power plug to allow the computer 1602 to be plugged into a wall socket or a power source to, for example, power the computer 1602 or recharge a rechargeable battery.

There can be any number of computers 1602 associated with, or external to, a computer system containing computer 1602, with each computer 1602 communicating over network 1630. Further, the terms "client," "user," and other appropriate terminology can be used interchangeably, as appropriate, without departing from the scope of the present disclosure. Moreover, the present disclosure contemplates that many users can use one computer 1602 and one user can use multiple computers 1602.

Figure 17:
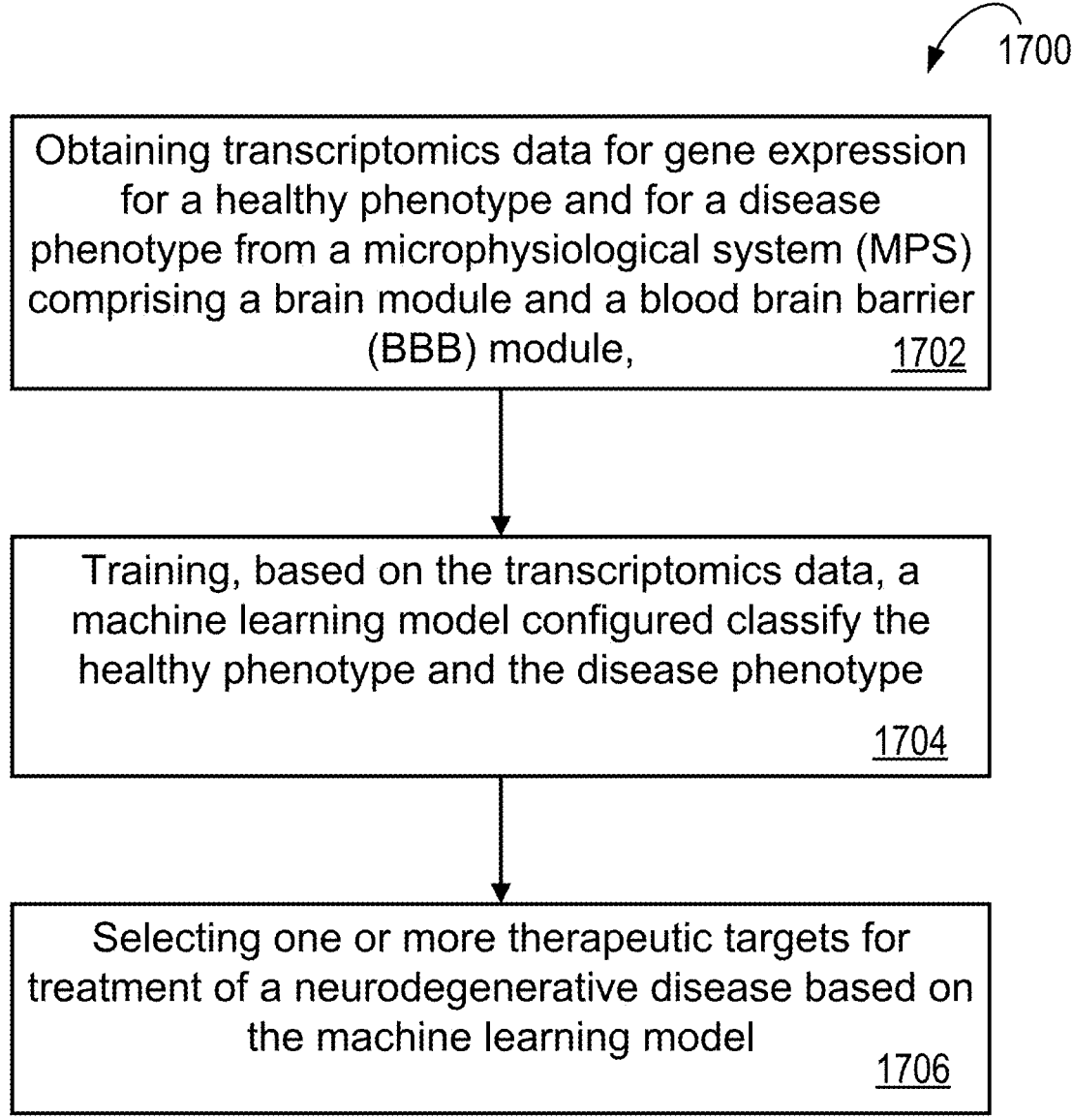
FIGS. 17-18 each show a flow diagram of an example process.

FIG. 17 is a flow chart illustrating an example process 1700 for determining a therapeutic target using an MPS (e.g., the NVUs previously described). The process 1700 includes obtaining (1702), from a microphysiological system (MPS) comprising a brain module and a blood brain barrier (BBB) module, transcriptomics data for gene expression for a healthy phenotype and for a disease phenotype. The process 1700 includes training (1704), based on the transcriptomics data, a machine learning model configured classify the healthy phenotype and the disease phenotype. The process 1700 includes selecting (1706) one or more therapeutic targets for treatment of a neurodegenerative disease based on the machine learning model. In some implementations, the process 1700 includes rank-ordering the one or more therapeutic targets based on one or more of, for each therapeutic target, a druggability, therapeutic evidence from a third party data source, a tissue specificity, safety or toxicity information, and a novelty. In some implementations, the process 1700 includes simulating target perturbations and evaluating one or more of the therapeutic targets using the machine learning model.

Figure 18:
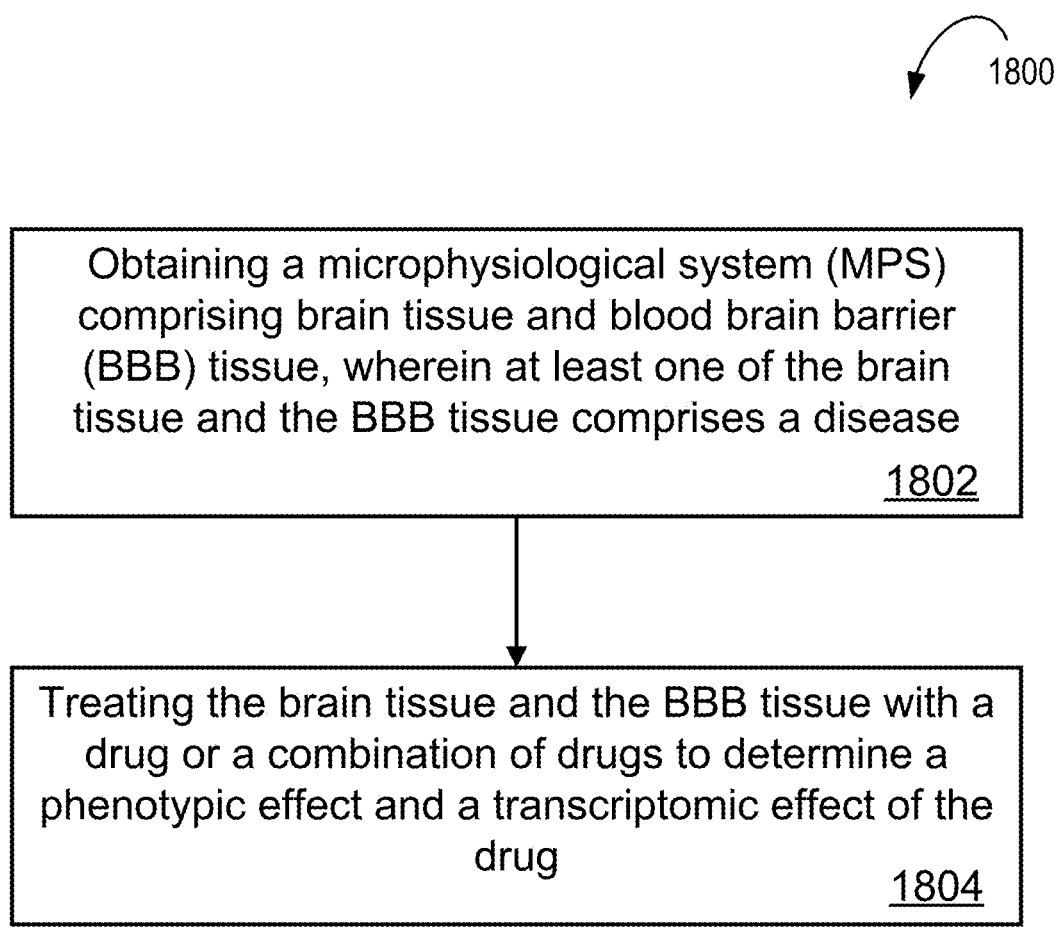

FIG. 18 is a flow chart illustrating an example process 1800 for determining a therapeutic target using an MPS (e.g., the NVUs previously described). The process 1800 includes obtaining (1802) a microphysiological system (MPS) comprising brain tissue and blood brain barrier (BBB) tissue, wherein at least one of the brain tissue and the BBB tissue comprises a disease. The process 1800 includes treating (1804) the brain tissue and the BBB tissue with a drug or a combination of drugs to determine a phenotypic effect and a transcriptomic effect of the drug.

In some implementations, the process 1800 includes determining one or more phenotypic markers related to the disease. In some implementations, the process 1800 includes perturbing the brain tissue and the BBB tissue using the drug. In some implementations, the process 1800 includes optimizing at least one kinetic parameter representing the brain tissue or the BBB tissue. In some implementations, the process 1800 includes relating the perturbation to the phenotypic effect and the transcriptomic effect based on the optimization.

In some implementations, the process 1800 includes determining one or more therapeutic targets for treatment of a neurodegenerative disease based on context-specific genome-scale metabolic model (GEM). In some implementations, the process 1800 includes generating the GEM by: determining a tissue type represented in the MPS, preserving a gene-protein-reaction association based on tissue-specificity data, and performing a metabolic simulation including the gene-protein-reaction association to validate the GEM. In some implementations, the one or more therapeutic targets comprise one or more of an mRNA, a protein, and a metabolite.

In the previous description, for the purposes of explanation, numerous specific details are set forth in order to provide a thorough understanding of the present disclosure. However, the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference is made in detail to implementations, examples of which are illustrated in the accompanying drawings. In the previous description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising" or "further including" in the foregoing description or following claims, what follows this phrase can be an additional step or entity, or a sub-step/sub-entity of a previously-recited step or entity.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A microphysiological system (MPS), comprising:
   at least one first inlet for receiving a fluid medium;
   a brain module comprising brain tissue;
   a blood-brain-barrier (BBB) module comprising BBB tissue, the BBB module configured to receive the fluid medium; and
   a crosstalk channel between the brain module and the BBB module, the crosstalk channel configured to promote a bidirectional crosstalk between the brain tissue and the BBB tissue in response to receiving the fluid medium at the BBB module, the bidirectional crosstalk configured for exchange of one or more of nutrients, signaling molecules, and drugs between the brain module and the BBB module.

2. The MPS of claim 1, wherein the crosstalk channel comprises neuron-glia and glia-BBB crosstalk.

3. The MPS of claim 1, wherein the brain module comprises a plurality of compartments, the plurality of compartments comprising a neuron culture well and a glia culture chamber.

4. The MPS of claim 1, wherein the brain tissue, the BBB tissue, or both the brain tissue and the BBB tissue are diseased with a neurodegenerative disease.

5. The MPS of claim 4, wherein the neurodegenerative disease is recreated from one of dopaminergic neurons or medium spiny neurons, astrocytes, pericytes, endothelial cells, microglia, oligodendrocytes, or a combination thereof.

6. The MPS of claim 4, wherein the neurodegenerative disease is induced using one or more of a neurotoxin and a dopamine depletion treatment.

7. The MPS of claim 4, wherein the neurodegenerative disease is introduced using tissue comprising one or more disease genotypes.

8. The MPS of claim 1, wherein the brain tissue of the brain module comprises one or more of human iPSC-derived neurons, microglia, and astrocytes.

9. The MPS of claim 1, wherein the BBB tissue of the BBB module comprises one or more of human brain microvascular endothelial cells (HBMECs), pericytes, and astrocytes.

10. The MPS of claim 1, further comprising a microelectrode array (MEA) comprising one or more electrodes, the MEA being configured to perform an electrophysiology measurement comprising one or more of a network bursting frequency, an interburst interval, a burst duration, one or more neuron spikes, a per burst $Ca^{2+}$ signaling, and a disease-relevant ion channel activity.

11. The MPS of claim 1, further comprising a sensor configured to measure one or more biomarkers from the fluid medium, the biomarkers including one or more of neuroinflammation biomarkers, antioxidant molecules, oxidative stress biomarkers, or reactive oxygen species biomarkers.

12. The MPS of claim 1, wherein the BBB module comprises a first medium channel and a second medium channel for receiving the fluid medium, and wherein the BBB tissue is in a BBB culture channel between the first medium channel and the second medium channel.

13. The MPS of claim 1, further comprising a first outlet for sampling the fluid medium from the BBB module, a second outlet for sampling a second fluid medium from the brain module, or both the first and second outlets.

14. The MPS of claim 1, further comprising:
   a first BBB medium channel on a first side of the BBB module and configured to flow the fluid medium in a first direction along the BBB tissue of the BBB module; and
   a second BBB medium channel on a second side of the BBB module opposite the first side, the second BBB medium channel configured to flow the fluid medium in a second direction along the BBB tissue of the BBB module; wherein the crosstalk channel is configured to promote a bidirectional crosstalk between the brain tissue and the BBB tissue in response to receiving the fluid medium at the BBB module from the first BBB medium channel or the second BBB medium channel.

* * * * *